US008372954B2

(12) United States Patent
Tanha et al.

(10) Patent No.: US 8,372,954 B2
(45) Date of Patent: Feb. 12, 2013

(54) PHAGE DISPLAY LIBRARIES OF HUMAN $V_H$ FRAGMENTS

(75) Inventors: Jamshid Tanha, Ottawa (CA); Joycelyn Entwistle, Winnipeg (CA); Saran Narang, Ottawa (CA); Michael Dan, Toronto (CA); Colin R. Mackenzie, Ottawa (CA); Howard Kaplan, Toronto (CA); Carole Grad, legal representative, Toronto (CA)

(73) Assignee: National Research Council of Canada, Ottawa (CA)

( * ) Notice: Subject to any disclaimer, the term of this patent is extended or adjusted under 35 U.S.C. 154(b) by 184 days.

(21) Appl. No.: 10/451,585

(22) PCT Filed: Dec. 21, 2001
(Under 37 CFR 1.47)

(86) PCT No.: PCT/CA01/01845
§ 371 (c)(1),
(2), (4) Date: Jan. 3, 2005

(87) PCT Pub. No.: WO02/051870
PCT Pub. Date: Jul. 4, 2002

(65) Prior Publication Data
US 2005/0164180 A1    Jul. 28, 2005

Related U.S. Application Data

(60) Provisional application No. 60/258,031, filed on Dec. 22, 2000.

(51) Int. Cl.
*C07K 16/00*        (2006.01)
*C40B 40/10*        (2006.01)
(52) U.S. Cl. .............. 530/387.1; 530/350; 530/386; 536/23.53; 536/23.1
(58) Field of Classification Search .............. 530/387.1, 530/350, 386; 536/23.53, 23.1
See application file for complete search history.

(56) References Cited

U.S. PATENT DOCUMENTS

| | | |
|---|---|---|
| 4,593,002 A | 6/1986 | Dulbecco |
| 4,683,195 A | 7/1987 | Mullis |
| 4,683,202 A | 7/1987 | Mullis |
| 4,754,065 A | 6/1988 | Levenson |
| 4,800,159 A | 1/1989 | Mullis |
| 5,223,409 A | 6/1993 | Ladner |
| 5,403,484 A | 4/1995 | Ladner |
| 5,571,698 A | 11/1996 | Ladner |
| 5,639,863 A | 6/1997 | Dan |
| 5,702,892 A | 12/1997 | Kehoe |
| 5,750,373 A | 5/1998 | Garrard |
| 5,759,808 A | 6/1998 | Casterman |
| 5,821,047 A | 10/1998 | Garrard |
| 5,837,500 A | 11/1998 | Ladner |
| 7,138,501 B2 * | 11/2006 | Ruben et al. .............. 530/388.23 |
| 7,264,963 B1 * | 9/2007 | Knappik et al. ........... 435/320.1 |

FOREIGN PATENT DOCUMENTS

| | | | |
|---|---|---|---|
| WO | WO 0029004 | | 5/2000 |
| WO | WO 01/18058 | * | 3/2001 |
| WO | WO 0118058 | | 3/2001 |

OTHER PUBLICATIONS

Hofstadter et al, Jrnl. Mol. Biol. (1999), 285, 805-815.*
Lang et al, Biochemistry, 2000, 39, 15674-685.*
Please note that the copies(133pages) are not included since the reference is cited in the specification.. It is assumed that applicants have the reference since some of the inventors are also the inventors of the above WO reference.*
Lauwereys, M., Arbabi, G. M., Desmyter, A., Kinne, J., Holzer, W., De Genst, E., Wyns, L., and Muyldermans, S. (1998). Potent enzyme inhibitors derived from dromedary heavy-chain antibodies. EMBO J. 17:3512-3520.
Hamers, C. C., Atarhouch, T., Muyldermans, S., Robinson, G., Hamers, C., Songa, E.B., Bendahman, N., and Hamers, R. (1993). Naturally occurring antibodies devoid of light chains. Nature 363:446-448.
Desmyter, A., Transue, T. R., Ghahroudi, M.A., Thi, M. H., Poortmans, F., Hamers, R., Muyldermans, S., and Wyns., L. (1996). Crystal structure of a camel single-domain VH antibody fragment in complex with lysozyme [see comments]. Nat. Struct. Biol. 3:803-811.
Padlan, E.A. (1994). Anatomy of the antibody molecule. Mol Immunol 31:169-217.
Chothia, C. and Lesk, A.M. (1987). Canonical structures for the hypervariable regions of immunoglobulins. J. Mol Biol 196:901-917.
Chothia, C., Novotny, J., Bruccoleri, R., and Karplus, M. (1985). Domain association in immunoglobulin molecules. The packing of variable domains. J Mol Biol 186:651-663.
Ward, E.S., Gussow, D., Griffiths, A.D., Jones, P. T., and Winter, G. (1989). Binding activities of a repertoire of single immunoglobulin variable domains secreted from *Escherichia coli* [see comments]. Nature 341:544-546.
Cai, X. and Garen, A. (1996). A melanoma-specific VH antibody cloned from a fusion phage library of a vaccinated melanoma patient. Proc Natl Acad Sci USA 93:6280-6285.
Sheriff, S. and Constantine, K. L. (1996). Redefining the minimal antigen-binding fragment [news; comment]. Nat Struct Biol 3:733-736.
Spinelli, S., Frenken, L. Bourgeois, D., de Ron, L., Bos, W., Verrips, T., Anguille, C., Cambillau, C., and Tegoni, M. (1996). The crystal structure of a llama heavy chain variable domain [letter][see comments]. Nat Struct Biol 3:752-757.

(Continued)

*Primary Examiner* — T. D. Wessendorf
(74) *Attorney, Agent, or Firm* — Wolf, Greenfield & Sacks, P.C.

(57) ABSTRACT

Phage display libraries are taught in which the recombinant phage population displays a plurality of potential binding fragments having preferred characteristics of solubility and/or intermolecular interaction. Also taught are methods of biasing display libraries to produce variants which more closely approximate the preferred characteristics of the parental binding fragment.

2 Claims, 16 Drawing Sheets

OTHER PUBLICATIONS

Davies, J. and Riechmann, L., (1994). "Camelising" human antibody fragments: NMR studies on VH domains. FEBS Lett 339:285-290.

Decanniere, K., Desmyter, A., Lauwereys, M., Ghahroudi, M. A., Muyldermans, S., and Wyns, L. (1999). A single-domain antibody fragment in complex with RNase A: non-canonical loop structures and nanomolar affinity using two CDR loops. Structure 7:361-370.

Muyldermans, S., Atarhouch, T., Saldanha, J., Barbosa, J.A., and Hamers, R. (1994). Sequence and structure of VH domain from naturally occurring camel heavy chain immunoglobulins lacking light chains. Protein Eng 7:1129-1135.

Vu, K.B., Ghahroudi, M.A., Wyns, L., and Muyldermans, S. (1997). Comparison of llama VH sequences from conventional and heavy chain antibodies. Mol Immunol 34:1121-1131.

Davies, J. and Riechmann, L., (1996b). Affinity improvement of single antibody VH domains: residues in all three hypervariable regions affect antigen binding. Immunotechnology 2:169-179.

Davies, J. and Riechmann, L. (1996a). Single antibody domains as small recognition units: design and in vitro antigen selection of camelized, human VH domains with improved protein stability. Protein Eng 9:531-537.

Morea, V., Tramontano, A., Rustici, M., Chothia, C., and Lesk, A.M. (1998). Conformations of the third hypervariable region in the VH domain of immunoglobulins. J Mol Biol 275:269-294.

Constantine, K.L., Goldfarb, V., Wittekind, M., Anthony, J., Ng, S. C., and Mueller, L. (1992). Sequential 1H and 15N NMR assignments and secondary structure of a recombinant anti-digoxin antibody VL domain, Biochemistry 31:5033-5043.

Constantine, K.L., Goldfarb, V., Wittekind, M., Friedrichs, M.S., Anthony, J., Ng, S. C., and Mueller, L. (1993). Aliphatic 1H and 13C resonance assignments for the 26-10 antibody VL domain derived from heteronuclear multidimensional NMR spectroscopy. J Biomol NMR 3:41-54.

Arabi, G. M., Desmyter, A., Wyns, L., Hamers, R., and Muyldermans, S. (1997). Selection and identification of single domain antibody fragments from camel heavy-chain antibodies. FEBS Lett 414:521-526.

Davies, J. and Riechmann, L. (1995). Antibody VH domains as small recognition units. Biotechnology NY 13:475-479.

Reiter, Y. LSchuck, P., Boyd, L. F., and Plaksin, D. (1999). An antibody single-domain phage display library of a native heavy chain variable region: isolation of functional single-domain VH molecules with a unique interface. J. Mol Biol 290:685-698.

Lowman, H. B., Bass, S. H., Simpson, N., and Wells, J.A. (1991). Selecting high-affinity binding proteins by monovalent phase dipslay. Biochemistry 30:10832-10838.

Nissim, A., Hoogenboom, H.R., Tomlinson, I.M., Flynn, G., Midgley, C., Lane, D., and Winter, G. (1994). Antibody fragments from a 'single pot' phase display library as immunochemical reagents. EMBO J 13:692-698.

Harrison, Jacqueline L., Screening of Phage Antibody Libraries, 1996 Methods in Enzymology. vol. 267.

Antibody Phage Display Technology and Its Applications, Hoogenboom, Hennie R. et al., 1998 lmmunotechnology 4 p. 1-20.

Cesareni G et al. Phage displayed peptide libraries, Comb Chem High Throughput Screen, Feb. 2, 1999(I):1-17.

Yip, YL et al, Epitope discovery using monoclonal antibodies and phage peptide libraries, Comb Chem High Throughput Screen, Jun. 2, 1999(3):125-38.

Rodi DJ et al, Phage-display technology-finding a needle in a vast molecular haystack, Curr Opin Biotechnol, Feb. 10, 1999(1): 87-93.

Riechmann L et al, Single Domain Antibodies:Comparison of Camel VH and Camelised Human VH Domains, Journal of Immunological Methods, Elsevier Science Publishers B.V., Amsterdam, NL, vol. 231, No. 1-2, Dec. 10, 1999, p. 25-38, XP004187632 ISSN 0022-1759, the whole document.

Tung, Wai Lin et al, A Modified Medium for efficient electrotransformation of E. coli TIG Apr. 1995 vol. 11 No. 4.

Dan, Michael D., Human-monoclonal antibody BT32/A6 and a Cell Cycle-independent glioma-associated surface antigen.

* cited by examiner

Figure 1

Structure of VH domain of human A6 antibody.

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| GAG | GTC | CAG | CTG | CAG | GAG | TCT | GGG | GGA | GGC | TTA | GTC | CAG | CCT |
| E | V | Q | L | Q | E | S | G | G | G | L | V | Q | P |

| 15 | 16 | 17 | 18 | 19 | 20 | 21 | 22 | 23 | 24 | 25 | 26 | 27 | 28 |
|---|---|---|---|---|---|---|---|---|---|---|---|---|---|
| GGG | GGG | TCC | CTG | AGA | CTC | TCC | TGT | TCA | GCC | TCT | GGA | TTC | ACC |
| G | G | S | L | R | L | S | C | S | A | S | G | F | T |

| 29 | 30 | 31 | 32 | 33 | 34 | 35 | 36 | 37 | 38 | 39 | 40 | 41 | 42 |
|---|---|---|---|---|---|---|---|---|---|---|---|---|---|
| TTC | AGT | AGC | TAT | GCT | ATG | CAC | TGG | GTC | CGC | CAG | GCT | CCA | GGG |
| F | S | S | Y | A | M | H | W | V | R | Q | A | P | G |

CDR1 spans positions 31–35 (S Y A M H)

| 43 | 44 | 45 | 46 | 47 | 48 | 49 | 50 | 51 | 52 | a | 53 | 54 | 55 |
|---|---|---|---|---|---|---|---|---|---|---|---|---|---|
| AAG | GGA | CTG | GAA | TAT | GTT | TCA | GCT | ATT | AGT | AGT | AAT | GGG | GGT |
| K | G | L | E | Y | V | S | A | I | S | S | N | G | G |

CDR2 begins at position 50

| 56 | 57 | 58 | 59 | 60 | 61 | 62 | 63 | 64 | 65 | 66 | 67 | 68 | 69 |
|---|---|---|---|---|---|---|---|---|---|---|---|---|---|
| AGC | ACA | TAC | TAC | GCA | GAC | TCC | GTG | AAG | GGC | AGA | TTC | ACC | ATC |
| S | T | Y | Y | A | D | S | V | K | G | R | F | T | I |

| 70 | 71 | 72 | 73 | 74 | 75 | 76 | 77 | 78 | 79 | 80 | 81 | 82 | a |
|---|---|---|---|---|---|---|---|---|---|---|---|---|---|
| TCC | AGA | GAC | AAT | TCC | AAG | AAC | ACT | CTG | TAT | CTT | CAA | ATG | AGC |
| S | R | D | N | S | K | N | T | L | Y | L | Q | M | S |

| b | c | 83 | 84 | 85 | 86 | 87 | 88 | 89 | 90 | 91 | 92 | 93 | 94 |
|---|---|---|---|---|---|---|---|---|---|---|---|---|---|
| AGT | CTG | AGA | GCT | GAG | GAC | ACG | GCT | GTG | TAT | TAC | TGT | GTG | AAA |
| S | L | R | A | E | D | T | A | V | Y | Y | C | V | K |

Figure 1 (continued)

| 95 | 96 | 97 | 98 | 99 | 100 | a | b | c | d | e | f | g | h |
|---|---|---|---|---|---|---|---|---|---|---|---|---|---|
| GAC | AGG | TTA | AAA | GTG | GAG | TAC | TAT | GAT | AGT | AGT | GGT | TAT | TAC |
| D | R | L | K | V | E | Y | Y | D | S | S | G | Y | Y |

<u>CDR3</u>

| i | j | k | l | m | n | o | 101 | 102 | 103 | 104 | 105 | 105 | 107 |
|---|---|---|---|---|---|---|---|---|---|---|---|---|---|
| GTT | TCT | CGG | TTC | GGT | GCT | TTT | GAT | ATC | TGG | GGC | CAA | GGG | ACA |
| V | S | R | F | G | A | F | D | I | W | G | Q | G | T |

| 108 | 109 | 110 | 111 | 112 | 113 |
|---|---|---|---|---|---|
| ACG | GTC | ACC | GTC | TCA | TCA |
| T | V | T | V | S | S |

Figure 2

Structure of V_H domain of human A6 antibody.

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| GAG | GTC | CAG | CTG | CAG | GCT | TCT | GGG | GGA | GGC | TTA | GTC | CAG | CCT |
| E | V | Q | L | Q | A | S | G | G | G | L | V | Q | P |

| 15 | 16 | 17 | 18 | 19 | 20 | 21 | 22 | 23 | 24 | 25 | 26 | 27 | 28 |
|----|----|----|----|----|----|----|----|----|----|----|----|----|----|
| GGG | GGG | TCC | CTG | AGA | CTC | TCC | TGT | GCT | GCC | TCT | GGA | TTC | ACC |
| G | G | S | L | R | L | S | C | A | A | S | G | F | T |

| 29 | 30 | 31 | 32 | 33 | 34 | 35 | 36 | 37 | 38 | 39 | 40 | 41 | 42 |
|----|----|----|----|----|----|----|----|----|----|----|----|----|----|
| TTC | AGT | AGC | TAT | GCT | ATG | CAC | TGG | GTC | CGC | CAG | GCT | CCA | GGG |
| F | S | S | Y | A | M | H | W | V | R | Q | A | P | G |

<u>CDR1</u> (residues 31–35: S Y A M H)

| 43 | 44 | 45 | 46 | 47 | 48 | 49 | 50 | 51 | 52 | a | 53 | 54 | 55 |
|----|----|----|----|----|----|----|----|----|----|---|----|----|----|
| AAG | GGA | CTG | GAA | TAT | GTT | TCA | GCT | ATT | AGT | AGT | AAT | GGG | GGT |
| K | G | L | E | Y | V | S | A | I | S | S | N | G | G |

<u>CDR2</u> starts at 50

| 56 | 57 | 58 | 59 | 60 | 61 | 62 | 63 | 64 | 65 | 66 | 67 | 68 | 69 |
|----|----|----|----|----|----|----|----|----|----|----|----|----|----|
| AGC | ACA | TAC | TAC | GCA | GAC | TCC | GTG | AAG | GGC | AGA | TTC | ACC | ATC |
| S | T | Y | Y | A | D | S | V | K | G | R | F | T | I |

| 70 | 71 | 72 | 73 | 74 | 75 | 76 | 77 | 78 | 79 | 80 | 81 | 82 | a |
|----|----|----|----|----|----|----|----|----|----|----|----|----|---|
| TCC | AGA | GAC | AAT | TCC | AAG | AAC | ACT | CTG | TAT | CTT | CAA | ATG | AAC |
| S | R | D | N | S | K | N | T | L | Y | L | Q | M | N |

| b | c | 83 | 84 | 85 | 86 | 87 | 88 | 89 | 90 | 91 | 92 | 93 | 94 |
|---|---|----|----|----|----|----|----|----|----|----|----|----|----|
| AGT | CTG | AGA | GCT | GAG | GAC | ACG | GCT | GTG | TAT | TAC | TGT | GCG | AAA |
| S | L | R | A | E | D | T | A | V | Y | Y | C | A | K |

Figure 2 (continued)

```
95   96   97   98   99   100  a    b    c    d    e    f    g    h
GAC  AGG  TTA  AAA  GTG  GAG  TAC  TAT  GAT  AGT  AGT  GGT  TAT  TAC
 D    R    L    K    V    E    Y    Y    D    S    S    G    Y    Y
                              CDR3 i    j    k    l    m    n    o   101  102  103  104  105  105  107
GTT  TCT  CGG  TTC  GGT  GCT  TTT  GAT  ATC  TGG  GGC  CAA  GGG  ACA
 V    S    R    F    G    A    F    D    I    W    G    Q    G    T 108  109  110  111  112  113
CAG  GTC  ACC  GTC  TCA  TCA
 Q    V    T    V    S    S
```

Figure 3

Structure of V<sub>H</sub> domain of human A6 antibody.

| 1 | 2 | 3 | 4 | 5 | 6 | 7 | 8 | 9 | 10 | 11 | 12 | 13 | 14 |
|---|---|---|---|---|---|---|---|---|---|---|---|---|---|
| GAG | GTC | CAG | CTG | CAG | GCT | TCT | GGG | GGA | GGC | TTA | GTC | CAG | CCT |
| E | V | Q | L | Q | A | S | G | G | G | L | V | Q | P |

| 15 | 16 | 17 | 18 | 19 | 20 | 21 | 22 | 23 | 24 | 25 | 26 | 27 | 28 |
|---|---|---|---|---|---|---|---|---|---|---|---|---|---|
| GGG | GGG | TCC | CTG | AGA | CTC | TCC | TGT | GCT | GCC | TCT | GGA | TTC | ACC |
| G | G | S | L | R | L | S | C | A | A | S | G | F | T |

| 29 | 30 | 31 | 32 | 33 | 34 | 35 | 36 | 37 | 38 | 39 | 40 | 41 | 42 |
|---|---|---|---|---|---|---|---|---|---|---|---|---|---|
| TTC | AGT | AGC | TAT | GCT | ATG | CAC | TGG | GTC | CGC | CAG | GCT | CCA | GGG |
| F | S | S | Y | A | M | H | W | V | R | Q | A | P | G |

CDR1: S Y A M H

| 43 | 44 | 45 | 46 | 47 | 48 | 49 | 50 | 51 | 52 | a | 53 | 54 | 55 |
|---|---|---|---|---|---|---|---|---|---|---|---|---|---|
| AAG | GGA | CTG | GAA | TAT | GTT | TCA | GCT | ATT | AGT | AGT | AAT | GGG | GGT |
| K | G | L | E | Y | V | S | A | I | S | S | N | G | G |

CDR2 starts at A I S S N G G

| 56 | 57 | 58 | 59 | 60 | 61 | 62 | 63 | 64 | 65 | 66 | 67 | 68 | 69 |
|---|---|---|---|---|---|---|---|---|---|---|---|---|---|
| AGC | ACA | TAC | TAC | GCA | GAC | TCC | GTG | AAG | GGC | AGA | TTC | ACC | ATC |
| S | T | Y | Y | A | D | S | V | K | G | R | F | T | I |

| 70 | 71 | 72 | 73 | 74 | 75 | 76 | 77 | 78 | 79 | 80 | 81 | 82 | a |
|---|---|---|---|---|---|---|---|---|---|---|---|---|---|
| TCC | AGA | GAC | AAT | GCC | AAG | AAC | ACT | CTG | TAT | CTT | CAA | ATG | AAC |
| S | R | D | N | A | K | N | T | L | Y | L | Q | M | N |

| b | c | 83 | 84 | 85 | 86 | 87 | 88 | 89 | 90 | 91 | 92 | 93 | 94 |
|---|---|---|---|---|---|---|---|---|---|---|---|---|---|
| AGT | CTG | AAA | CCA | GAG | GAC | ACG | GCT | GTG | TAT | TAC | TGT | GCG | AAA |
| S | L | K | P | E | D | T | A | V | Y | Y | C | A | K |

Figure 3 (continued)

```
95   96   97   98   99   100  a    b    c    d    e    f    g    h
GAC  AGG  TTA  AAA  GTG  GAG  TAC  TAT  GAT  AGT  AGT  GGT  TAT  TAC
 D    R    L    K    V    E    Y    Y    D    S    S    G    Y    Y
                                 CDR3 i    j    k    l    m    n    o   101  102  103  104  105  105  107
GTT  TCT  CGG  TTC  GGT  GCT  TTT  GAT  ATC  TGG  GGC  CAA  GGG  ACA
 V    S    R    F    G    A    F    D    I    W    G    Q    G    T 108  109  110  111  112  113
CAG  GTC  ACC  GTC  TCA  TCA
 Q    V    T    V    S    S
```

Figure 4

Structure of VH domain of human A6 antibody. The mutated nucleotides spanning residues 7-48 to remove the recombination site are in bold and underlined.

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| GAG | GTC | CAA | TTA | CAG | GAA | AGT | GGT | GGC | GGA | CTG | GTG | CAA | CCA |
| E | V | Q | L | Q | E | S | G | G | G | L | V | Q | P |

| 15 | 16 | 17 | 18 | 19 | 20 | 21 | 22 | 23 | 24 | 25 | 26 | 27 | 28 |
|----|----|----|----|----|----|----|----|----|----|----|----|----|----|
| GGA | GGA | TCC | CTG | AGA | CTC | TCC | TGT | TCA | GCC | TCT | GGA | TTC | ACC |
| G | G | S | L | R | L | S | C | S | A | S | G | F | T |

| 29 | 30 | 31 | 32 | 33 | 34 | 35 | 36 | 37 | 38 | 39 | 40 | 41 | 42 |
|----|----|----|----|----|----|----|----|----|----|----|----|----|----|
| TTC | AGT | AGC | TAT | GCT | ATG | CAC | TGG | GTC | CGC | CAG | GCT | CCA | GGG |
| F | S | S | Y | A | M | H | W | V | R | Q | A | P | G |
|  |  | CDR1 |  |  |  |  |  |  |  |  |  |  |  |

| 43 | 44 | 45 | 46 | 47 | 48 | 49 | 50 | 51 | 52 | a | 53 | 54 | 55 |
|----|----|----|----|----|----|----|----|----|----|---|----|----|----|
| AAG | GGA | CTG | GAA | TAT | GTT | TCA | GCT | ATT | AGT | AGT | AAT | GGG | GGT |
| K | G | L | E | Y | V | S | A | I | S | S | N | G | G |
|  |  |  |  |  |  |  |  | CDR2 |  |  |  |  |  |

| 56 | 57 | 58 | 59 | 60 | 61 | 62 | 63 | 64 | 65 | 66 | 67 | 68 | 69 |
|----|----|----|----|----|----|----|----|----|----|----|----|----|----|
| AGC | ACA | TAC | TAC | GCA | GAC | TCC | GTG | AAG | GGC | AGA | TTC | ACC | ATC |
| S | T | Y | Y | A | D | S | V | K | G | R | F | T | I |

| 70 | 71 | 72 | 73 | 74 | 75 | 76 | 77 | 78 | 79 | 80 | 81 | 82 | a |
|----|----|----|----|----|----|----|----|----|----|----|----|----|---|
| TCC | AGA | GAC | AAT | TCC | AAG | AAC | ACT | CTG | TAT | CTT | CAA | ATG | AGC |
| S | R | D | N | S | K | N | T | L | Y | L | Q | M | S |

| b | c | 83 | 84 | 85 | 86 | 87 | 88 | 89 | 90 | 91 | 92 | 93 | 94 |
|---|---|----|----|----|----|----|----|----|----|----|----|----|----|
| AGC | CTG | AGA | GCT | GAG | GAC | ACG | GCT | GTG | TAT | TAC | TGT | GTG | AAA |
| S | L | R | A | E | D | T | A | V | Y | Y | C | V | K |

Figure 4 (continued)

| 95 | 96 | 97 | 98 | 99 | 100 | a | b | c | d | e | f | g | h |
|---|---|---|---|---|---|---|---|---|---|---|---|---|---|
| GAC | AGG | TTA | AAA | GTG | GAG | TAC | TAT | GAT | AGT | AGT | GGT | TAT | TAC |
| D | R | L | K | V | E | Y | Y | D | S | S | G | Y | Y |

CDR3

| i | j | k | l | m | n | o | 101 | 102 | 103 | 104 | 105 | 105 | 107 |
|---|---|---|---|---|---|---|---|---|---|---|---|---|---|
| GTT | TCT | CGG | TTC | GGT | GCT | TTT | GAT | ATC | TGG | GGC | CAA | GGG | ACA |
| V | S | R | F | G | A | F | D | I | W | G | Q | G | T |

| 108 | 109 | 110 | 111 | 112 | 113 |
|---|---|---|---|---|---|
| ACG | GTC | ACC | GTC | TCA | TCA |
| T | V | T | V | S | S |

Figure 8

Structure of modified VH domain of human A6 antibody showing substitutions at position 44, 45, 47, 93 and 94  The *NheI* site is underlined.

| 1 | 2 | 3 | 4 | 5 | 6 | 7 | 8 | 9 | 10 | 11 | 12 | 13 | 14 |
|---|---|---|---|---|---|---|---|---|----|----|----|----|----|
| GAG | GTC | CAG | CTG | CAG | GAG | TCT | GGG | GGA | GGC | TTA | GTC | CAG | CCT |
| E | V | Q | L | Q | E | S | G | G | G | L | V | Q | P |

| 15 | 16 | 17 | 18 | 19 | 20 | 21 | 22 | 23 | 24 | 25 | 26 | 27 | 28 |
|----|----|----|----|----|----|----|----|----|----|----|----|----|----|
| GGG | GGG | TCC | CTG | AGA | CTC | TCC | TGT | TCA | GCC | TCT | GGA | TTC | ACC |
| G | G | S | L | R | L | S | C | S | A | S | G | F | T |

| 29 | 30 | 31 | 32 | 33 | 34 | 35 | 36 | 37 | 38 | 39 | 40 | 41 | 42 |
|----|----|----|----|----|----|----|----|----|----|----|----|----|----|
| TTC | AGT | AGC | TAT | GCT | ATG | CAC | TGG | GTC | CGC | CAG | GCT | CCA | GGG |
| F | S | S | Y | A | M | H | W | V | R | Q | A | P | G | position 31-35 underlined: S Y A M H  (CDR1)

| 43 | 44 | 45 | 46 | 47 | 48 | 49 | 50 | 51 | 52 | a | 53 | 54 | 55 |
|----|----|----|----|----|----|----|----|----|----|---|----|----|----|
| AAG | GAA | CGT | GAA | GGT | GTT | TCA | GCT | ATT | AGT | AGT | AAT | GGG | GGT |
| K | E | R | E | G | V | S | A | I | S | S | N | G | G | position 50-55 underlined: A I S S N G G (CDR2)

| 56 | 57 | 58 | 59 | 60 | 61 | 62 | 63 | 64 | 65 | 66 | 67 | 68 | 69 |
|----|----|----|----|----|----|----|----|----|----|----|----|----|----|
| AGC | ACA | TAC | TAC | GCA | GAC | TCC | GTG | AAG | GGC | AGA | TTC | ACC | ATC |
| S | T | Y | Y | A | D | S | V | K | G | R | F | T | I |

| 70 | 71 | 72 | 73 | 74 | 75 | 76 | 77 | 78 | 79 | 80 | 81 | 82 | a |
|----|----|----|----|----|----|----|----|----|----|----|----|----|---|
| TCC | AGA | GAC | AAT | TCC | AAG | AAC | ACT | CTG | TAT | CTT | CAA | ATG | AGC |
| S | R | D | N | S | K | N | T | L | Y | L | Q | M | S |

| b | c | 83 | 84 | 85 | 86 | 87 | 88 | 89 | 90 | 91 | 92 | 93 | 94 |
|---|---|----|----|----|----|----|----|----|----|----|----|----|----|
| AGT | CTG | AGA | GCT | GAG | GAC | ACG | GCT | GTG | TAT | TAC | TGT | GCA | GCA |
| S | L | R | A | E | D | T | A | V | Y | Y | C | A | A |

Figure 8 (continued)

| 95 | 96 | 97 | 98 | 99 | 100 | a | b | c | d | e | f | g | h |
|---|---|---|---|---|---|---|---|---|---|---|---|---|---|
| GAC | AGG | TTA | AAA | GTG | GAG | TAC | TAT | GAT | AGT | AGT | GGT | TAT | TAC |
| D | R | L | K | V | E | Y | Y | D | S | S | G | Y | Y |

CDR3

| i | j | k | l | m | n | o | 101 | 102 | 103 | 104 | 105 | 105 | 107 |
|---|---|---|---|---|---|---|---|---|---|---|---|---|---|
| GTT | TCT | CGG | TTC | GGT | GCT | TTT | GAT | ATC | TGG | GGC | CAA | GGG | ACA |
| V | S | R | F | G | A | F | D | I | W | G | Q | G | T |

| 108 | 109 | 110 | 111 | 112 | 113 |
|---|---|---|---|---|---|
| ACG | GTC | ACC | GTC | TCA | TCA |
| T | V | T | V | S | S |

Figure 10

A6VH sequence for the A6VH-L1 library

- 5 mutations ( in bold)
- Randomization at 100i-n

```
GAG GTC CAA TTA CAA GCT AGT GGT GGC GGA CTG GTG CAA CCA GGA GGT TCC CTG
 E   V   Q   L   Q   A₆  S   G   G   G   L   V   Q   P   G   G   S   L

AGA CTC TCC TGT GCT GCC TCT GGA TTC ACC TTC AGT AGC TAT GCT ATG CAC TGG GTC
 R   L   S   C   A₂₃ A   S   G   F   T   F   S   S   Y   A   M   H   W   V

CGC CAG GCT CCA GGG AAG GGA CTG GAA TAT GTT TCA GCT ATT AGT AGT AAT GGG
 R   Q   A   P   G   K   G   L   E   Y   V   S   A   I   S   S   N   G

GGT AGC ACA TAC TAC GCA GAC TCC GTG AAG GGC AGA TTC ACC ATC TCC AGA GAC
 G   S   T   Y   Y   A   D   S   V   K   G   R   F   T   I   S   R   D

AAT TCC AAG AAC ACT CTG TAT CTT CAA ATG AAC AGT CTG AGA GCT GAG GAC ACG
 N   S₇₄ K   N   T   L   Y   L   Q   M   N₈₂ₐ S   L   R₈₃ A₈₄ E   D   T

GCT GTG TAT TAC TGT GCG AAA GAC AGG TTA AAA GTG GAG TAC TAT GAT AGT AGT
 A   V   Y   Y   C   A₉₃ K   D   R   L   K   V   E   Y   Y   D   S   S

GGT TAT TAC 6 [NNA/C] TTT GAT ATC TGG GGC CAA GGG ACA CAG GTC ACC GTC TCC
 G   Y   Y  6[   N   ]  F   D   I   W   G   Q   G   T   Q₁₀₃ V   T   V   S

TCA
 S
```

Figure 11

A6VH sequence for the A6VH-L1a library

- 5 mutations ( in bold)
- 100i-n deleted
- Randomization at 95-100h with 50% base doping at each position.

```
GAG GTC CAA TTA CAA GCT AGT GGT GGC GGA CTG GTG CAA CCA GGA GGT TCC CTG
 E   V   Q   L   Q   A₆  S   G   G   G   L   V   Q   P   G   G   S   L

AGA CTC TCC TGT GCT GCC TCT GGA TTC ACC TTC AGT AGC TAT GCT ATG CAC TGG GTC
 R   L   S   C   A₂₃ A   S   G   F   T   F   S   S   Y   A   M   H   W   V

CGC CAG GCT CCA GGG AAG GGA CTG GAA TAT GTT TCA GCT ATT AGT AGT AAT GGG
 R   Q   A   P   G   K   G   L   E   Y   V   S   A   I   S   S   N   G

GGT AGC ACA TAC TAC GCA GAC TCC GTG AAG GGC AGA TTC ACC ATC TCC AGA GAC
 G   S   T   Y   Y   A   D   S   V   K   G   R   F   T   I   S   R   D

AAT TCC AAG AAC ACT CTG TAT CTT CAA ATG AAC AGT CTG AGA GCT GAG GAC ACG
 N   S₇₄ K   N   T   L   Y   L   Q   M   N₈₂ₐ S   L   R₈₃ A₈₄ E   D   T

GCT GTG TAT TAC TGT GCG AAA 14 [50%NNA/C] TTT GAT ATC TGG GGC CAA GGG ACA
 A   V   Y   Y   C   A₉₃ K   14[      N      ] F   D   I   W   G   Q   G   T
CAG GTC ACC GTC TCC TCA
 Q₁₀₈ V   T   V   S   S
```

PHAGE DISPLAY LIBRARIES OF HUMAN $V_H$ FRAGMENTS

RELATED APPLICATIONS

The present application claims benefit of priority to provisional patent application Ser. No. 60/258,031, filed Dec. 22, 2000, and international patent application number PCT/CA01,01845, entitled "Phage Display Libraries of Human $V_H$ Fragments", filed Dec. 21, 2001, which are incorporated by reference herein in their entirety.

FIELD OF THE INVENTION

The present invention relates to combinatorial libraries including phage display libraries which display single domain heavy chain binding fragments having preferred characteristics of solubility.

BACKGROUND OF THE INVENTION

Developments in antibody engineering and recombinant DNA technology have made it possible to generate forms of recombinant antibody fragments which, in many ways, are functional substitutes of larger intact immunoglobulin molecules. Single heavy domain antibody fragments ("dAb") have been the subject of several reports in the patent and scientific literature. The literature reports efforts to generate phage display libraries of such fragments for biopanning against a target ligand.

U.S. Pat. No. 5,702,892 ('892) discloses a phage display library constructed in an M13 derived expression vector, in which recombinant phage of the library contain a polynucleotide encoding a fusion protein which comprises a phage coat protein and an immunoglobulin heavy chain binding-fragment. The heavy-chain binding-fragment spans from a position upstream of CDR1 to a position downstream of CDR3. '892 describes that the DNA sequence encoding the CDR3 region and/or the CDR1 region may be randomly varied so that the population of phage expresses a series of potential heavy chain binding domains for panning against the target ligand. U.S. Pat. No. 5,759,808 discloses a phage display library comprising a population of phage based on random variation of a cDNA sequence obtained from lymphocytes of camelids previously immunized with target antigens. Camelid heavy chain antibodies occur naturally, in a composition of about 45%, as heavy chain dimers. Heavy chain antibodies specific for a target antigen may be generated by immunizing a member of the camelid species with the target antigen (see Lauwereys et al. (1998) The EMBO J. 17, 3512-3520).

Hamers-Casterman et al. (1993) Nature 363, 446-448 report that camelid heavy chain antibodies are naturally more hydrophilic at amino acid residues at locations 44, 45 and 47 (Kabat numbering system), in FR2, which corresponds to the surface where they normally contact the VL domain Another salient feature of a camelid $V_H$ is that it generally has a comparatively longer CDR3 with a high incidence of cysteines and thus may form, via paired cysteines in CDR1 and CDR3, exposed loops, which are more amenable to binding into cavities such as the active site of enzymes and antibodies (Desmyter et al. (1996) Nat. Struct. Biol. Vol. 3, No. 9, p. 803). However, it has been questioned whether single domain antibodies with desired affinities can be generated with such configurations in the absence of prior immunization, i.e. with a naïve library (Lauwereys et al. (1998) supra).

The present invention discloses advances in the technology related to creating libraries containing immunoglobulin-like proteins that specifically bind target ligands eg. antigens.

SUMMARY OF THE INVENTION

According to one aspect, the invention is directed to a library for expression of immunoglobulin heavy chain domains, said library comprising a repertoire of nucleic acid sequences each encoding a polypeptide comprising a $V_H$, said $V_H$ comprising a CDR and any one, two, three or four, or five, amino acids from a group comprising 6-A, 23-A, 82a-N, 93-A and 108-Q, said repertoire comprising a diversity of sequences which differ from one another at least in a subsequence coding for part of the CDR so as to provide nucleic acid encoding a repertoire of polypeptides comprising V differing at least in said CDR and comprising at least one amino acid of said group.

In addition to a library of nucleic acid molecules, the term expression library is understood to specifically include a phage, viral, bacterial or other cell surface display library, a ribosome display library or any other functional nucleic acid expression system which permits the expression products to be screened.

According to another aspect, the invention is directed to a method for generating a $V_H$ expression library having a diversity of CDR sequences, said method comprising: providing expression vectors, said vectors comprising a nucleic acid sequence which encodes a polypeptide comprising a $V_H$, said $V_H$ comprising a CDR and any one, two, three or four, or five, amino acids from a group comprising 6-A, 23-A, 82a-N, 93-A and 108-Q; introducing by mutagenesis a diversity of CDR sequences into said $V_H$ nucleic acid sequence; and recovering an expression library having a diversity of binding activities.

According to another aspect, the invention is directed to an expression library which expresses polypeptides comprising Vs, said library comprising a set of framework regions carrying a diversity of CDR sequences, said library having a diversity of binding activities, said frame work regions comprising one, two, three or four, or five, amino acids from a group comprising 6-A, 23-A, 82a-N, 93-A and 108-Q. The invention is also directed to a method of identifying a polypeptide comprising a $V_H$, which binds to a target ligand, the method comprising the steps of screening polypeptide members of this immediately aforementioned expression library for their respective ability to bind to the target ligand; and identifying at least one polypeptide member which binds to the target ligand.

According to another aspect, the invention is directed to a polypeptide comprising a $V_H$, said polypeptide derived from a library according to any of the preceding paragraphs.

The invention is directed to a population of variants of at least one parental $V_H$ ligand-binding molecule (dAb), wherein said parental $V_H$ ligand-binding molecule comprises an immunoglobulin $V_H$ binding fragment comprising, at least in substantial part, at least the framework (FR) regions of the immunoglobulin $V_H$ fragment depicted FIG. 2, wherein said variants comprise at least in substantial part, the FR regions of the immunoglobulin $V_H$ fragment depicted FIG. 2, including at least one (and preferably all) of amino acid residues, 6, 23, 82a, 93, and 108, and differ from said parental ligand-binding molecule in amino acid residues constituting at least part of at least one of the CDRs of said parental ligand-binding molecule: Preferably said population of variants is constituted by one or more combinatorial libraries of such variants, for example, protein arrays, phage display libraries, ribosome display libraries etc.

It is to be understood that the variants may (though not necessarily) form part of another structure or molecule, for example in the case of phage display, part of the coat protein of the phage. Accordingly, the term variant is used broadly to refer to variants of the essential molecule (a ligand-binding molecule) when forming part of another structure or molecule (eg. as in phage display or ribosome display) or when independent of any such combination, eg. in the case of protein arrays whose members may not be associated with individual supporting structures/molecules.

In a particularly preferred embodiment said parental $V_H$ ligand binding molecule and said variants comprise each of amino acid residues 6, 23, 82a, 93 and 108, depicted in FIG. 2 and more preferably each of amino acid residues 6, 23, 74, 82a, 83, 84, 93, and 108 depicted in FIG. 3. More preferably, said parental $V_H$ ligand binding molecules and said variants include the entirety of the FR regions the parental $V_H$ ligand molecule depicted in FIG. 2 or 3, optionally subject to one or more additions, deletions and/or substitutions, (preferably conservative amino acid substitutions) which, if they do not improve, preferably at least do not adversely affect the solubility properties of said variants. Optionally, said parental $V_H$ ligand binding molecules and variants additionally include, the entirety of the CDR1 and CDR2 depicted in FIG. 2 or 3, optionally subject to one or more additions, deletions and/or substitutions (preferably conservative amino acid substitutions) which, if they do not improve, preferably at least do not adversely affect the solubility properties of said variants. In a particularly preferred embodiment, said parental $V_H$ ligand molecule and said variants, additionally comprise, the entirety of CDR3 of the parental $V_H$ ligand binding molecule depicted in FIG. 2 with the exception of amino acids 100i to 100n, which are randomized to create said population of variants subject only to one or more additions, deletions, and/or substitutions, (preferably conservative amino acid substitutions) which, if they do not improve, preferably at least do not adversely affect the solubility properties of said variants. In another embodiment, said parental $V_H$ ligand binding molecule and said variants comprise one or more amino substitutions relative to FIG. 2, including any combinations thereof.

In a further preferred embodiment nucleotides corresponding to amino acid residues 3-16 are optimized to remove a putative recombination site.

For purposes herein, it is to be understood that an adverse affect on the solubility properties is to be assessed in terms of the percentage of dimer and higher aggregate forms, relative to monomer, as determined by size exclusion chromatography (i.e. the respective areas under the peaks representing monomer, dimer and higher aggregate forms, as illustrated in FIG. 5).

In another aspect, the invention is directed to a ligand-binding molecule or variant which has been identified as binding to a target ligand by screening a combinatorial library of the invention for one or more ligand-binding molecules which specifically recognize said target ligand. The invention is also directed more generally to any specific such ligand-binding molecule which is derived from such combinatorial library of the invention. It is understood herein that such specific ligand-binding molecule may be directly obtained from such a library or may be indirectly derived, for example, through the course of further antibody engineering or other modification steps (eg. creating fragments, derivatives, a secondary library, etc) using a ligand-binding molecule directly or indirectly obtained from such library. It also understood that the invention excludes known ligand-binding molecules. In one embodiment of this aspect of the invention the target ligand is a cancer antigen.

FIGS. 2, 3 and 4 depict variations, more fully described below, on the preferred immunoglobulin $V_H$ ligand binding fragment and/or nucleic acid construct depicted in FIG. 1. FIG. 1 describes a wild-type parental immunoglobulin $V_H$ binding fragment derived from human monoclonal antibody BT32/A6 (hereinafter referred to as "A6") partially described in U.S. Pat. No. 5,639,863 (hereinafter referred to as the '863 patent). As described in our co-pending application PCT/CA00/01027, the contents of which are hereby incorporated by reference, A6 has preferred solubility and other characteristics which lend themselves well to the creation of libraries, including naive libraries, of various types of human immunoglobulin fragments including dAbs as more fully described below. Accordingly, A6, and in particular, as more fully described below, at least a substantial part of the framework (FR) regions of the A6 $V_H$ fragment depicted in FIG. 2, alone or in combination with features of its CDR3, provides a useful departure point, in the form of a parental ligand-binding molecule, for the randomization or partial randomization of amino acid residues which tend to play a predominant role in ligand-binding, namely the CDR regions of the heavy chain and particularly the CDR3 of the heavy chain. As more fully described below, the nucleic acid changes (removal of the recombination site) relative to A6 wild-type FIG. 1) reflected in FIG. 4 may be incorporated into FIGS. 2 and 3 respectively.

The combinatorial library of the invention may be generated by phage display. In a preferred embodiment of one aspect of the invention, the invention is directed to a phage display library displaying a plurality of different variants of a parental $V_H$ ligand-binding molecule, wherein said parental ligand-binding molecule comprises an immunoglobulin $V_H$ binding fragment comprising, at least in substantial part, at least the FR regions of the immunoglobulin $V_H$ fragment depicted in FIG. 3 including at least one of amino acid residues 6, 23, 74, 82a, 83, 84, 93 and 108, and wherein said variants are encoded by nucleic acid sequences which vary from the nucleic acid sequence encoding said parental ligand-binding molecule in a subsequence (at least one) encoding at least part of one of the CDRs of said parental ligand-binding molecule, preferably the CDR3, whereby said plurality of variants comprise at least, in substantial part, the FR regions of the immunoglobulin $V_H$ fragment depicted in FIG. 3, including at least one of said amino acid residues and are differentiated, at least in part, by amino acid variations encoded by variations in said subsequence.

In a preferred embodiment, in addition to substantial preservation and optional improvement of the FR regions of A6, the A6-based parental ligand molecule comprises (and therefore preserves within members of the library), in substantial part (subject to at least partial randomization of selected regions of one of the CDRs (preferably the CDR3), to create binding diversity within the library, one or more of the CDR regions of the A6 $V_H$ fragment. In a further preferred embodiment, at least the length of the wild-type $V_H$ CDR3 (23 amino acids) and preferably also elements of its amino acid composition, is preserved or at least partially preserved (approximately 16-23 amino acids and more particularly 18 to 23 amino acids). Optionally the CDR3 may also be lengthened by approximately 1 to 10 residues. The library may optionally have representation of binding molecules having CDR3s of varying lengths.

It is known that a dAb molecule, due to the removal of its light chain partner, tends to, in most, if not all cases, aggregate, in varying degrees due to the "sticky" nature of the VL interface. This stickiness is attributable, at least in part, to the hydrophobic nature of the $V_H$ residues at this interface. This stickiness results in substantial dimer and/or multimer formation which may reduce, on the whole, the solubility characteristics of members of the library. Accordingly, in a further preferred aspect of the invention A6 $V_H$ amino acid residues at the VL interface are substituted by residues which tend to minimize aggregate formation, for example, hydrophilic amino acids, including one or more of the highlighted substitutions reflected in FIG. 8, relative to FIG. 1.

Alternatively, in yet a further preferred embodiment of the invention, more fully described below, such substitutions are not fixed within the entire population of the library, but are introduced by randomizing or partially randomizing various A6 $V_H$ amino acid residues, particularly including FR residues, among the residues at the interface. (see for example, Padlan et al "Anatomy of the Antibody Molecule" Molecular Immunology Vol. 31, p 169-217, Table 25 for itemization and related discussion of these residues).

Particularly in the case of larger size libraries, for example those generated by ribosome display, it is possible to introduce diversity in one or more FR regions containing amino acid residues identified herein as important for improving solubility properties, in addition to one or more regions affecting the specificity of the dAb, eg. the $V_H$ CDR3 and CDR1.

Alternatively, in yet a further preferred embodiment of the invention, FR regions, other than, or in addition to, modifications to the VL interface (FR2) may be modified by at least partial randomization, for example, one or both of FR1 (one or more of residues 4 to 21) and FR4 (one or more of residues 100o to 113) to improve, on the whole, the solubility characteristics of members of the library (for example, biasing at least some and preferably all of one or both of these sets of residues [at least 70% or more], preferably 90% in favour of the parental amino acid constitution to achieve 10% randomization).

In the case of A6 dAb fragments, it has been found that recombination events within the nucleic acid sequence encoding the $V_H$ binding fragment tend to result in deletions yielding shorter molecules, with possible compromise in binding characteristics. Thus, in a further preferred aspect of the invention nucleic acid sequences which promote such recombination events (at putative recombination sites) are substituted, to oppose this tendency, preferably in a manner that does not result in an amino acid change. These changes may be incorporated, for example, into the nucleotide sequences encoding the parental $V_H$ ligand-binding molecule depicted in FIG. 2 or 3.

In particularly preferred aspects, the present invention provides a heterogeneous population of genetic packages (eg. phage) having a genetically determined outer surface protein, wherein the genetic packages collectively display a plurality of different, preferably human (i.e. having substantial identity, preferably at least 80% homology to human framework and other conserved regions) $V_H$ ligand-binding fragments, each genetic package including a nucleic acid construct coding for a fusion protein which comprises at least a portion of the outer surface protein and a variant of at least one soluble parental ligand-binding fragment preferably derived from or having a substantial part of the FR regions of the amino acid sequence identified in one of FIG. 2 or 3 (or a sequence at least 80%, preferably 85 to 100%, more preferably 90-100%, homologous (% identity) thereto), including at least one and preferably all of amino acid residues 6, 23, 82a, 93 and 108 depicted in FIG. 2 or 3, wherein the variant $V_H$ ligand-binding fragments preferably span from a position upstream of an immunoglobulin heavy chain CDR1 to a position downstream of CDR3 (preferably including substantially all of FR1 and/or FR4), and wherein at least part of a CDR, preferably the CDR3, is a randomly generated variant of a CDR of said parental $V_H$ ligand binding-fragment and wherein the fusion protein is preferably expressed in the absence of an immunoglobulin light chain whereby the variant $V_H$ ligand-binding fragments are, on the whole, better adapted to be or better capable of being expressed as soluble proteins. Various combinations of 2, 3 and 4 substitutions relative to wild-type A6 at amino acid residues 6, 23, 82a, 93 and 108 are also contemplated by the invention.

In yet another embodiment of the invention, by biasing the amino acid constitution, preferably on an individual amino acid by amino acid basis, in favor of the wild-type or parental amino acid constitution, even portions of the parental ligand-binding molecule that are randomized in favor of generating variability in the variant binding fragments can be engineered to maintain favorable solubility characteristics of the parental binding domain. In one embodiment of the invention, a portion of the construct encoding at least part of the CDR3 is biased or partially biased in favor of the parental amino acid constitution.

In a further preferred embodiment, the parental $V_H$ binding-fragment naturally has a long CDR3 that is amenable to forming exposed loops for binding into cavities. In a most preferred embodiment, the parental $V_H$ ligand-binding fragment is built on a human framework or is adapted from or adaptable to a human framework.

In another preferred embodiment, the preferred binding region of the variants (corresponding to the randomized or partially randomized part of the CDR3) is located in carboxy terminal region of the CDR3.

In summary, according to a preferred embodiment of the invention, a substantial part of the amino acid sequence identified in FIG. 2, preferably including at least part of the CDR3, supplies the preferred amino acid constitution of the various preferred parental ligand-binding molecules, such that a population of variant heavy chain ligand-binding molecules built on this framework of amino acids are on the whole better adapted to be or better capable of being expressed as soluble proteins.

Generally, the importance of amino acid residues 6, 23, 82a, 93, and 108, shown in FIG. 2, particularly when all five are combined, is that they can be used to significantly augment the solubility properties of a parental $V_H$ ligand binding fragment, preferably one, like A6, that has useful solubility properties to begin with, to produce a library of dAb variants for paining against a target ligand, said variants on the whole being better adopted to be or better capable of being expressed as soluble proteins.

BRIEF DESCRIPTION OF THE DRAWINGS

The invention will now be described with reference to the drawings, wherein:

FIG. 1 is a sequence diagram showing the A6 $V_H$ ligand-binding molecule from which we construct parental $V_H$ ligand binding molecules according to the invention.

FIG. 2 is a sequence diagram showing a preferred parental $V_H$ ligand-binding molecule (A6$V_H$-L1) according to the invention, incorporating amino acid substitutions E6A, S23A, S82aN, 93A and T108Q.

FIG. 3 is a sequence diagram showing the A6$V_H$-L2 ligand-binding molecule according to the invention, incorporating 3 additional amino acid substitutions at positions 74, 83 and 84.

FIG. 4 is a sequence diagram showing the A6$V_H$ ligand-binding molecule (encoded by A6 chi (−)) according to the invention, in which nucleic acids corresponding to amino acids 3 to 16 of A6 have been modified to remove a putative recombination site, leaving the amino acid constitution of A6 unchanged.

Figures 5, 5A, 5B, 5C:
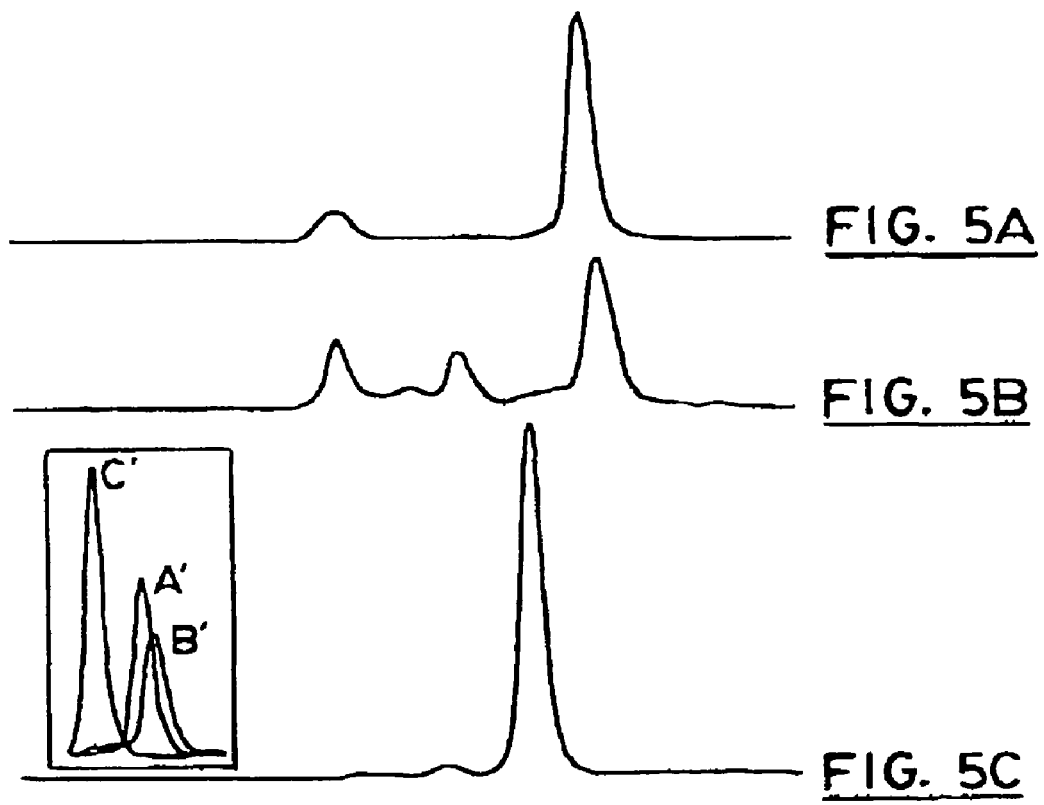
FIG. 5 is a size exclusion chromatogram of A6$V_H$-L1 dAb following IMAC purification comparing A6$V_H$-L1 (plot A) to wildtype A6$V_H$ (plot B) and showing a much greater proportion of monomer (represented by the largest peak). Plot C represents a camelized version of A6 with amino acid substitutions of positions 44, 45, 47 and 94 as described herein and in the literature.
Figure 6:
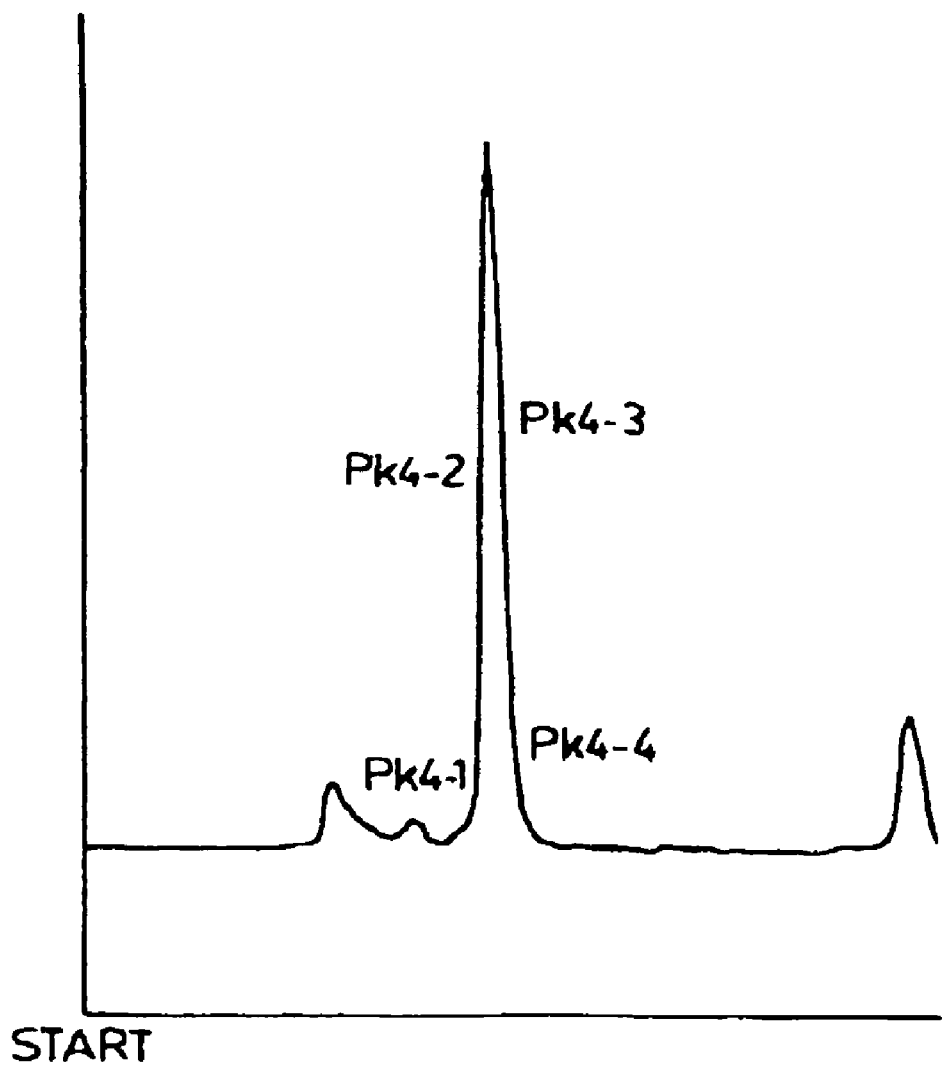
FIG. 6 is a size exclusion chromatogram of Yst9.1-L3-9, which was used for binding against Yst9.1 scFv, depicted in FIG. 7.
Figure 7:
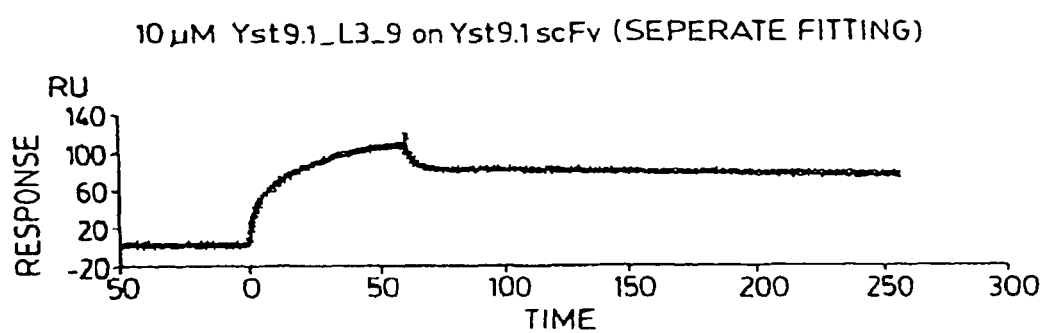
FIG. 7 is a sensorgram showing the binding of 10 (M Yst9.1-L3-9 binding to immobilized Yst9.1 scFv. The control surface (BSA) data has been subtracted from the active surface (Yst9.1) data in this sensorgram. The rate constants were calculated by separate fitting of the association (fit shown) and dissociation data to a 1:1 interaction model.

FIG. 8 is a sequence diagram showing amino acid substitutions for optional camelization according to one embodiment of the invention.

FIG. 9 is a diagrammatic representation of vector, SJFI used to create the vector into which the library may be cloned.

FIG. 10 is a sequence diagram depicting the library construction strategy for library A6$V_H$-L1.

FIG. 11 is a sequence diagram depicting the library construction strategy for library A6$V_H$-L1a.

DETAILED DESCRIPTION OF PREFERRED EMBODIMENTS

In a preferred embodiment, the invention is directed to a population of genetic packages having a genetically determined outer surface protein including genetic packages which collectively display a plurality of different ligand-binding molecules in association with the outer surface protein, each package including a nucleic acid construct coding for a fusion protein which is at least a portion of the outer surface protein and a variant of at least one soluble parental ligand-binding molecule derived from or having the amino acid sequence identified in FIG. 2 (or a sequence preferably at least 80% homologous to the framework and conserved regions thereof), which includes at least one and preferably all of amino acids 6, 23 82a, 94 and 108 shown in FIG. 2 (or conservative substitutions of those residues which, if they do not improve, at least do not adversely affect the solubility properties of said parental $V_H$ ligand binding molecule), wherein at least part of the construct, preferably including at least part of the CDR3 identified in FIG. 2, encodes or is biased in favor of encoding, the amino acid constitution of the parental ligand binding fragment such that the plurality of different ligand-binding domains are on the whole better adapted to be or better capable of being expressed as soluble proteins. The variant $V_H$ ligand-binding molecules are preferably characterized by a CDR3 having 16 to 33 amino acids.

Preferably, the replicable genetic package is a recombinant phage and the heterogeneous population of replicable genetic packages collectively constitute a phage display library.

In a further embodiment, the VL interface is engineered to avoid hydrophobic amino acids. In another embodiment, the VL interface is engineered for amino acids, which form weak interactions. In another embodiment the parental ligand binding molecule has a camelid type VL interface. In another embodiment, at least one of the VL interface amino acids are randomized or partially randomized in the construction of the library.

Preferably the potential $V_H$ binding fragments include the entire FR1 through to FR4 regions, although it is to be understood that partial deletions, for example, within CDR2, are contemplated to be within the scope of the invention.

Preferably, CDR3s of a variety of different lengths from 16 to 33 amino acids are predominantly represented among the potential $V_H$ binding fragments. Preferably CDR3s of a variety of different lengths, from 18 to 28 amino acids, or from 20 to 25, or from 18 to 23, amino acids are predominantly represented in the library. In a preferred embodiment of the invention, the parental $V_H$ ligand-binding fragment is built on a human framework and preferably is the parental $V_H$ ligand-binding fragment identified in FIG. 2 which has a CDR3 of 23 amino acids in length.

More importantly, the invention encompasses a phage display library which is constructed using a parental $V_H$ ligand-binding molecule derived from native A6$V_H$ (FIG. 1), or is built on any framework which is at least 80% (preferably 85%, more preferably 90 to 95%) homologous to the framework and other conserved regions of a fully human $V_H$ chain. The invention also contemplates that the parental $V_H$ binding-fragment, though not human, is adapted (egg. humanized) or adaptable (egg. to be adapted after selection of preferred binders) to a human framework.

In another embodiment, the invention also contemplates the random, biased or fixed occurrence of features disclosed in the camelid literature, for example pairable cysteines in CDR1 and CDR3 (optional) and/or the substitution of hydrophilic amino acids at least one of positions 44, 45, and 47 and preferably also positions 93 and 94 (Kabat numbering system).

In a most preferred embodiment of the invention, the parental ligand-binding molecule is a $V_H$ fragment derived from a human IgM heavy chain, and preferably comprises FR1 through FR4 of the $V_H$ chain. A partial sequence of the preferred antibody BT32/A6 (A6) is disclosed in U.S. Pat. No. 5,639,863, incorporated herein by reference. The entire sequence is supplied now in FIG. 1.

In FIG. 1, the CDR regions are demarcated. The amino acid residue numbers in FIG. 1 and throughout the disclosure refer to the Kabat numbering system (Kabat et al. 1991, Sequences of Proteins of Immunological Interest, publication No. 91-3242, U.S. Public Health Services, NIH, Bethesda Md.) except in the sequence listings and where explicitly stated or otherwise implied. FIG. 1 corresponds to SEQ. ID. NO. 1 (nucleic acid) and SEQ. ID. NO. 2 (amino acid). FIG. 1 demarcates and labels regions CDR1 (corresponding to SEQ. ID. NO. 3), CDR2 (SEQ. ID. NO. 4) and CDR3 (SEQ. ID. NO. 5).

The A6 framework provides preferred solubility characteristics for creating dAb libraries. The term preferred solubility characteristics, as used herein, refers to at least one of the several, often correlated, characteristics including good yield, expression as a soluble product (as opposed to inclusion bodies) within the periplasm of the host organism, eg. *Escherichia Coli*, and a reduced tendency to dimerize and form other aggregates.

The term "$V_H$" is used to refer to the variable heavy chain domain and variants thereof made by routine skill in the art, including known forms, truncated and fusion protein forms thereof, which variants retain its essential binding characteristics. This term is used interchangeably with the terms such as $V_H$ binding fragment, $V_H$ ligand binding fragment, dAb and immunoglobulin $V_H$ fragment, to which the same meaning is ascribed.
Figure 9:
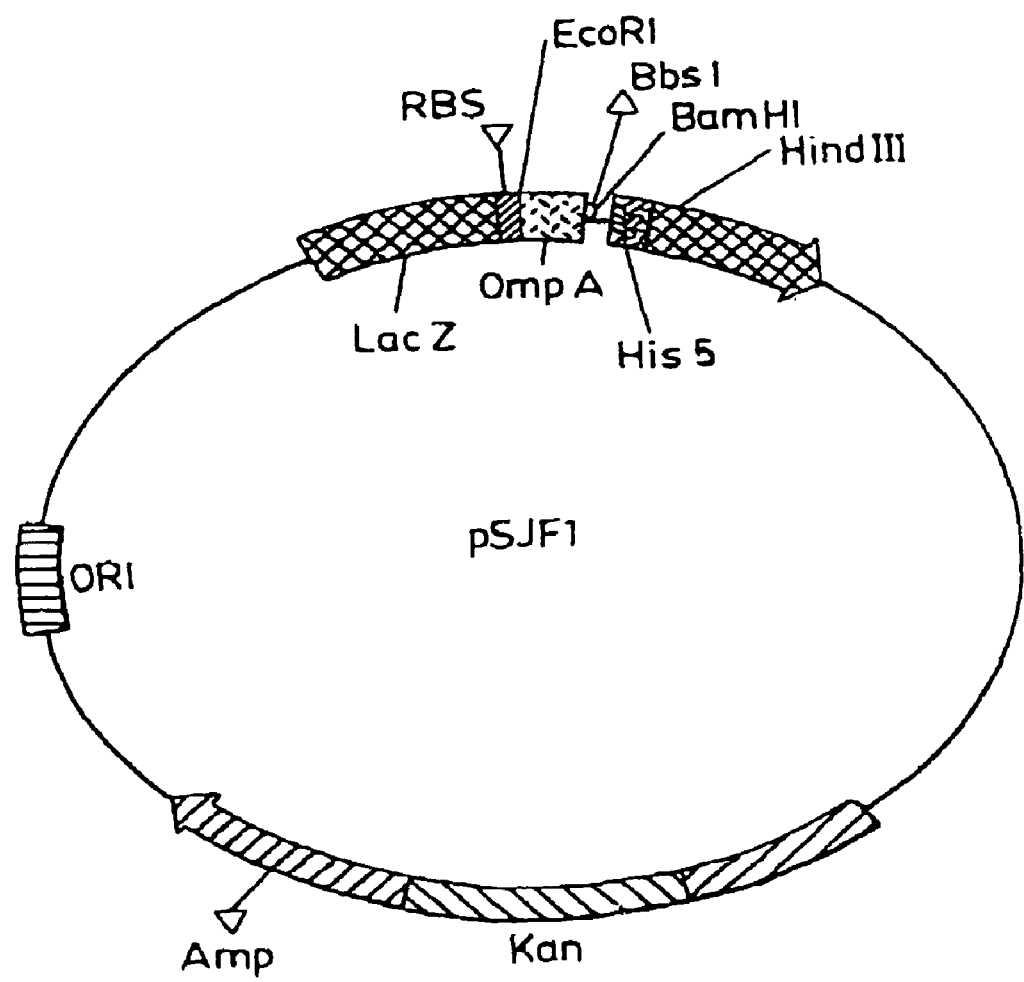

The term "subsequence" is used to refer to a subset of nucleotides within a referenced nucleic acid sequence and includes a single nucleotide and consecutive and non-consecutive nucleotides within a sequence of greater than two consecutive nucleotides.

The terms "polypeptide", "peptide" and "protein", unless the context implies otherwise, are used interchangeably herein, to refer to polymers of amino acid residues of any length.

The term "combinatorial library" is used herein to refer to a set of molecules, typically belonging to a defined (narrowly or broadly) class comprising a substantial number of potentially useful variants, wherein the variations in the molecule represent a complete or partial set of permutations or combinations of at least some constituent elements of a reference molecule, which is typically a template or "parental" molecule, or simply the class itself. For clarity, in the case of polypeptides and nucleic acids, the constituent elements are amino acids and nucleic acid bases, respectively.

As used herein, the phrase "in substantial part" refers to variations relative to a referenced molecule which do not significantly impair the "functionality" of that molecule. In the case of the parental ligand-binding molecule and variants thereof functionality refers primarily to the solubility and binding characteristics of the molecule. Such variations (i.e. the referenced molecule in substantial part) can be tested systematically to assess their impact. In the case of framework regions, in contrast to CDR regions, due to the substantial conservation of the framework amino acid residues, a substantial part of the framework would preferably refer to at least 80% identity of the amino acid residues and more preferably an 85 to 100% identity, and even more preferably at least a 90% identity of the amino acid residues. However, it is understood that each of the previous percentages could be relaxed to discount instances where the absence of identity in a given residue, is due to a well recognized conservative amino acid substitution, or where a particular class of functionality is noted, e.g. hydrophilic, if the substitution is with a residue of the same class. In the case of CDR residues, these numbers could be considerably even more relaxed, and includes 50 to 100% homology, and all incremental percentages and all ranges of percentages therebetween. The term "in substantial part", in reference to portions of framework and CDR regions, also contemplates the possibility of additions and deletions in those regions which preferably do not impact the solubility and binding characteristics of the ligand-binding molecule in question.

The term ligand-binding fragment is used broadly to define the whole or any part of an antibody that is capable of specifically binding to any ligand, in the broadest sense of the term ligand.

An A6-based human heavy domain ligand-binding-fragment is well suited for the development of a combinatorial library (optionally a phage display library) that is used to generate soluble binding fragments that are useful for human diagnosis and therapy (due to limited HAMA response). These phage display libraries are used to selectively generate molecular probes that specifically interact with a ligand, including without limitation, natural and synthetic molecules and macromolecules and can be used in vitro (i.e., a diagnostic) and in vivo (i.e., a diagnostic and/or therapeutic) as indicators, inhibitors and immunological agents. The types of natural and synthetic molecules and macromolecules include but are not limited to: antibodies and fragments thereof; enzymes; cell receptors; proteins, polypeptides, peptides; polynucleotides, oligonucleotides; carbohydrates such as polysaccharides, oligosaccharides, saccharides; lipids; organic-based and inorganic-based molecules such as antibiotics, steroids, hormones, pesticides, herbicides, dyes, polymers.

Conventional antibodies such as those found in human or murine species are composed of two identical light chains and two identical heavy chains. The combining sites of these antibodies are formed by association of the variable domains of both chains. This association is mediated through hydrophobic interactions at the interface. Structural and biochemical studies have shown that the heavy chain variable domain ($V_H$) provides most of the antigen-contacting residues (Padlan, 1994) (Chothia & Lesk, 1987) (Chothia, Novotny, et al., 1985). This finding has formed the basis for the development of single heavy domain antibodies (dAbs)—recombinant antigen binding fragments consisting of only the $V_H$ (Ward, Gussow, et al., 1989) (Cai & Garen, 1996). However, in the absence of their VL partners, $V_H$s have been found to be insoluble, presumably because of the exposed hydrophobic VL interface (Ward, Gussow, et al., 1989). Heavy chain antibodies, found in camelids (Hamers, Atarhouch, et al., 1993) (Sheriff & Constantine,), lack light chains and as a result have variable domains that reflect the absence of a VL partner. Single domain antibodies derived from these antibodies are highly soluble and the structural basis of solubility has been partially elucidated. First, conserved human/murine interface residues such as Val37, Gly44, Leu45 and Trp47 are generally replaced in heavy chain antibodies by tyrosine or phenylalanine, glutamate, arginine or cysteine, and glycine, respectively. These mutations increase the hydrophilicity of the VL interface either by non-polar to polar substitutions or, in a more subtle way, by inducing local conformational changes (Desmyter, Transue, et al., 1996) (Spinelli, Frenken, et al.,). This explanation is supported by experiments in which an insoluble human $V_H$ was made soluble by introducing the aforementioned mutations at positions 44, 45 and 47 (Davies & Riechmann, 1994). Second, in the solved structures of two camel dabs, the CDR3s fold back on the $V_H$ surface, masking a significant surface area of the VL interface (Desmyter, Transue, et al., 1996)(Decanniere, Desmyter, et al., 1999).

Several other features of $V_H$Hs are noteworthy. One is the frequent occurrence of the cysteine residues in CDR1 and CDR3 (Muyldermans, Atarhouch, et al., 1994) (Lauwereys, Arbabi, et al., 1998 (Vu, Ghahroudi, et al., 1997). While the location of the CDR1 cysteine is typically fixed at position 33, that of the CDR3 cysteine varies. These two residues form a disulfide linkage between CDR1 and CDR3 (Desmyter, Transue, et al., 1996) (Davies & Riechmann, 1996). In the crystal structure of a dAb-lysozyme complex, the disulfide linkage imparts rigidity on the CDR3 loop which extends out of the combining site and penetrates deep into the active site of lysozyme (Desmyter, Transue, et al., 1996). A second feature is the longer average length of the $V_H$H CDR3, relative to human or murine $V_H$s (Muyldermans, Atarhouch, et al., 1994). A longer CDR3, which is a feature of A6, increases the antigen binding surface and, to some extent, compensates for the absence of the antigen binding surface provided by the VL in conventional antibodies (Desmyter, Transue, et al., 1996). A third feature is the absence of the CDR3 salt linkage that is typically present in conventional antibodies and formed by arginine or lysine residues at position 94 and aspartate at position 101 (Desmyter, Transue, et al., 1996) (Muyldermans, Atarhouch, et al., 1994) (Spinelli, Frenken, et al., 1996) (Davies & Riechmann, 1996) (Chothia & Lesk, 1987) (Morea, Tramontano, et al., 1998).

As antigen binding fragments, dAbs are an attractive alternative to scFvs because of their much smaller size and the fact that they demonstrate affinities comparable to those demonstrated by scFvs (Ward, Gussow, et al., 1989) (Spinelli, Frenken, et al., 1996) (Lauwereys, Arbabi, et al., 1998) (Davies & Riechmann, 1995) (Arbabi, Desmyter, et al., 1997) (Reiter, Schuck, et al., 1999). Smaller size is an advantage in applications requiring tissue penetration and rapid blood clearance. Smaller molecules also offer a tremendous advantage in terms of structural studies (Davies & Riechmann, 1994) (Constantine, Goldfarb, et al., 1992 (Constantine, Goldfarb, et al., 1993).

Phage antibody library construction is much simpler and more efficient if single domain antibodies (dabs) are used instead of Fabs or single chain Fvs. Randomization can be introduced at a much higher percentage of CDR positions without exceeding practical library size. The problem of shuffling original VL-$V_H$ pairings is also avoided. Camelid phage dAb libraries constructed from the $V_H$H repertoire of camels immunized with target antigens have performed well (Arbabi, Desmyter, et al., 1997) (Lauwereys, Arbabi, et al., 1998) (Decanniere, Desmyter, et al., 1999). However, construction of libraries from immunized camels presents obvious problems. In addition, the non-human nature of products from these libraries limits their usefulness. Synthetic dAb libraries (Davies & Riechmann, 1995) (Reiter, Schuck, et al., 1999), particularly those based on a human $V_H$ framework, alleviate these problems.

As described in detail in Example 1, a dAb phage display library, according to the invention was constructed by randomizing positions 100i-100n of the parental $V_H$ ligand binding fragment identified in FIG. 2 (A6$V_H$-L1).

The actual library size was 2.4×10⁸ with 6.4×10⁷ possible sequences. The sequences of 27 clones randomly picked from the unpanned library confirmed the integrity of the library (Table 1).

TABLE 1

Sequences of the randomized region (100i-n) of randomly picked clones from the A6$V_H$-L1a library.

| | |
|---|---|
| SEQ ID NO: 1 | DQFTHS |
| SEQ ID NO: 2 | SSMYGN |
| SEQ ID NO: 3 | IKMQQN |
| SEQ ID NO: 4 | SVDARD |
| SEQ ID NO: 5 | VSRFGA |
| SEQ ID NO: 6 | GLGSPK |
| SEQ ID NO: 7 | IDAKWA |
| SEQ ID NO: 8 | VSRFGA |
| SEQ ID NO: 9 | HCLPDG |
| SEQ ID NO: 10 | RWR?VP |
| SEQ ID NO: 11 | VSRFGA |
| SEQ ID NO: 12 | LECEGC |
| SEQ ID NO: 13 | RNVGAL |
| SEQ ID NO: 14 | RRSDYL |
| SEQ ID NO: 15 | CVRGAE |
| SEQ ID NO: 16 | SPSLAA |
| SEQ ID NO: 17 | HASGRS |
| SEQ ID NO: 18 | GYMCSL |
| SEQ ID NO: 19 | HNKDLA |
| SEQ ID NO: 20 | LADLYM |
| SEQ ID NO: 21 | WRRAHE |
| SEQ ID NO: 22 | SDLFAR |
| SEQ ID NO: 23 | VSRFGA |
| SEQ ID NO: 24 | RYRHST |
| SEQ ID NO: 25 | ARLAGP |
| SEQ ID NO: 26 | SYRPYL |
| SEQ ID NO: 27 | VVLGNS |

As shown in FIG. 5, this potential $V_H$ ligand binding fragment shown has a substantially improved percentage of monomer relative to A6 wild-type.

The A6$V_H$-L1 library was panned against the anti-FLAG IgG M-2, H11 scFv and Brucella scFv.

M-2 Results

Three rounds of panning were performed. Twenty one clones from rounds 2 and 3 were sequenced (Table 2). The motif recognized by M-2 is XYKXXD. As we observed previously with the camelized A6$V_H$ library, the epitope was preferentially positioned at the C-terminus of the randomized region with the D residue of non-randomized FDI sequence forming part of the epitope. As shown in Table, the sequences of the M-2 binders identified by phage ELISA reasonably reproduce the motif recognized by M-2.

TABLE 2

Sequences of M-2 binders identified by phage ELISA.

| Sequence | # of clones |
|---|---|
| (A) deleted constructs | |
| EVQLQAS----- SGYYEDDYRLFDIWGQGTQVTVSS | 6 |
| EVQLQASGGGLVQP----- GYYDSSGYYKDLDTRFDIWGQGTQVTVSS | 1 |
| EVQLQASGGGLVQPGGSLRLS----- RLKVEYYDSSYYGDHYKWFDIWGQ GTQVTVSS | 1 |
| (B) Full length constructs (CDR3 only) | |
| DRLKVEYYDSSGYYRNEYKEFDI | 1 |
| DRLKVEYYDSSGYYVDEYKSFDI | 1 |
| DRLKVEYYDSSGYYAGRYKDFDI | 1 |
| DRLKVEYYDSSGYYRSDYKRFDI | 1 |
| DRLKVEYYDSSGYYASHYKDFDI | 1 |
| DRLKVEYYDSSGYYVDGYKDFDI | 1 |
| DRLKVEYYDSSGYYTADYKMFDI | 1 |
| DRLKVEYYDSSGYYDMDYKTFDI | 1 |
| DRLKVEYYDSSGYYKS?YKSFDI | 1 |
| DRLKVEYYDSSGYYDYKSQDFDI | 1 |
| DRLKVEYYDSSGYYKNWDSTFDI | 1 |
| DRLKVEYYDSSGYYKDWDSSFDI | 1 |
| DRLKVEYYDSSGYYKDGDSFFDI | 1 |

H11 Results

Three rounds of panning were performed in each instance. No deleted sequences were observed for either antigen.

Twenty-one H11 binders were sequenced. The sequence FSSP is present in 13 of the 21 H11 binders (Table 3).

TABLE 3

CDR3 sequences H11 binders identified by phage ELISA. The randomized region is shown in bold.

| CDR3 | # of clones |
|---|---|
| (A) H11 scFv | |
| DRLKVEYYDSSG--YSFSSPFDI | 7 |
| DRLKVEYYDSSGYYYDFSSPFDI | 3 |
| DRLKVEYYDSSGYYNLFSSPFDI | 1 |
| DRLKVEYYDSSGYYSEFSSPFDI | 1 |

TABLE 3-continued

CDR3 sequences H11 binders identified by phage ELISA. The randomized region is shown in bold.

| CDR3 | # of clones |
|---|---|
| DRLKVEYYDSSGYYSDFSSPFDI | 1 |
| DRLKVEYYDSSGYYTDMSWEFDI | 1 |
| DRLKVEYYDSSGYYDLGSWEFDI | 1 |
| DRLKVEYYDSSGYYDYVSWEFDI | 1 |
| DRLKVEYYDSSGYYDWGSWEFDI | 1 |
| DRLKVEYYDSSGYYDG?TWDFDI | 1 |
| DRLKVEYYDSSGYYWEGSGLFDI | 1 |
| DRLKVEYYDSSGYYIWYSGLFDI | 1 |
| DRLKVEYYDSSGYYSSWASAFDI | 1 |

*Brucella* scFv (Yst9.1)

Clones obtained by panning against Yst9.1 scFv were selected for expression. Two clones had VSRFGA sequence. The VSRFGA dAb was designated Yst9.1-L3-9.

The VSRFGA clone was expressed in good yield (approximately 18 mg/liter of bacterial culture) and was characterized by BIACORE.

Yst9.1-L3-9 dAb Binding to Immobilized Yst9.1 scFv

Following IMAC, the dAb was purified by Superdex 75 size exclusion chromatography prior to BIACORE analysis. It gave an elution profile that was similar to the parent A6$V_H$-L1 molecule (FIG. 6).

For the determination of binding kinetics and affinities, the purified dAb was injected over active (1800 RU of Yst9.1) and reference surfaces (9400 RU of BSA) to generate the sensorgram and constants presented in FIG. 7. The Yst9.1 surface was regenerated with 10 mM HCl (6 sec contact). All proteins were immobilized on CM5 chips by amine coupling. A 2000 RU $H_{11}$ scFv surface was also used as a reference. The dAb did not bind to BSA. The subtracted data, using the BSA surface as a reference, for dAb binding to Yst9.1 scFv fit quite well to a 1:1 interaction model. A KD of 117 nM was calculated.

According to another embodiment of the invention, the parental ligand-binding fragment has additional amino acid substitutions at VL interface which reduce the tendency to aggregation attributable to the "stickiness" of the $V_H$ dAb at this interface. For example, substitutions at positions 44, 45 and 47 relative to the wild-type A6$V_H$ (FIG. 1) are illustrated in FIG. 8.

According to another preferred embodiment of the invention, the parental ligand-binding fragment has a long CDR3.

In a particularly preferred embodiment, the library is constructed using the A6$V_H$-L1 parental $V_H$ ligand binding molecule as a template and preserves the entire length of this CDR3 and, additionally, at least one of positions 44, 45, 47 and 94 (and preferably all) is altered, (preferably including 44 or 45) to camelid type residues.

Davies and Riechmann (1995) constructed a camelized dAb library by randomizing CDR3 amino acid residues but the library was ten times larger and yielded anti-hapten dAbs with dissociation constants in the range of 100400 nM. However, the isolated anti-protein dAbs had weak affinity (Davies & Riechmann, 1995) (Davies & Riechmann, 1996). Therefore, a smaller library such as the one constructed here may therefore contain only weak anti-protein dAbs. The isolation of such dAbs would be difficult with monovalent display (Lowman, Bass, et al., 1991). In a phage vector format the dAb are displayed 3-5 copies and therefore there is potential for avidity which increases the likelihood of isolating weak binders (Nissim, Hoogenboom, et al., 1994).

Additional embodiments of the randomization strategy for the libraries of the invention, are described below.

The present inventors have also found a method of enhancing the probability that the binding fragments displayed in the library have characteristics which approximate the desired solubility characteristics found in the wild type binding fragment. During construction of the library, nucleotides of the variable region are added in a step-wise addition and by selecting a nucleotide ratio which is biased in favor of producing amino acids which reflect the DNA of the parental or wild type species.

Thus, a method for biasing a library in favor of obtaining selected percentages of wild type amino acid residues is achieved by creating residue substitutions by using different spiking levels of the various dNTPs as described below. When creating a phage library, the randomization of amino acids is often achieved by DNA synthesis. A primer is annealed next to DNA encoding for the variable region, and nucleotides are randomly added to synthesize randomized variable regions. Normally, at the step of synthesizing the DNA used to produce the variable region of the phage library, one uses a nucleotide ratio of 1:1:1:1, which generates a totally random variable region. By the present method, during synthesis of the variable region, the likelihood of achieving affinity or other desirable traits found in the wild type as follows. At each step of adding a nucleotide to the DNA variable region, one selects a dNTP ratio which is biased in favor of producing amino acids which reflect the DNA of the parental (wild type) species.

Table 4 charts particular amino acid residues or sequences of residues and preferred types of amino acid substitutions according to various examples of the invention to be defined hereafter. The selection of amino acids for randomization or partial randomization is based on adopting one or more of a variety of approaches including one of more of the following:

1. universal recognition of wild-type amino acids through a broad-based biasing in favour of the wild-type amino acids in one or more regions of interest (approximately 10%-90% biasing) in order to maintain the characteristics of the parental $V_H$ ligand-binding molecule;
2. selective recognition of amino acids that are important to maintain as wild-type through biasing (approximately 10-100%) in order maintain conserved or strategic regions of amino acid residues of the parental $V_H$ ligand-binding molecule; and
3. recognition of selected amino acids as important for intermolecular interaction and biasing those amino acids to wild-type and amino acids of the same type.

TABLE 4

| Amino Acid Residue #s | Description of Various Preferred Amino Acid Constitutions |
|---|---|
| a. At least one of 100a-100h, preferably at each position of 100a-100h | Randomize;<br>At least approximately 10% biasing in favor of wild-type amino acids;<br>At least approximately 50% biasing in favor of wild-type amino acids;<br>At least approximately 90% biasing in favor of wild-type amino acids;<br>Randomize, but bias 100f to wild-type (approximately 10-100%) |

TABLE 4-continued

| Amino Acid Residue #s | Description of Various Preferred Amino Acid Constitutions |
|---|---|
| b. At least one amino acid of: 100a-100b and 100g-100h preferably at each position of 100a-100b and 100g-100h | Randomize; Randomize with bias to wild-type (approximately 10-100%), preferably at least approximately 50% wild-type, alternatively at least approximately 90% wild-type amino acids; Randomize with bias to one of the amino acids selected from the group consisting of tyrosine, histidine, glutamine, asparagine, lysine, aspartic acid and glutamic acid (approximately 10-100%) |
| c. At least one of 100b-100g, preferably at each position of 100b-100g | Randomize; Delete; |
| d. 100a-100h | Random additions of up to 10 amino acids; Random deletions of up to 7 amino acids; |
| e. 95-100o | Randomize; Random additions of up to 10 amino acids; Random deletions of up to 7 amino acids; |
| f. At least one of 95-100, preferably at each position of 95-100 | Randomize; Randomize with bias to wild-type (approximately 10-100%), preferably at least approximately 50% wild-type, or preferably at least approximately 90% wild-type amino acids; Invariant (primer spans this region) |
| g. 101-102 conserved amino acids | Invariant (primer spans this region) N/A |
| i. At least one amino acid of 100a-100b, 100g-100h and 100l-100o, preferably at each position of 100a-100b, 100g-100h and 100l-100o | Randomize with bias to wild-type (approximately 10-100%), preferably at least approximately 50% wild-type, more preferably at least approximately 90% wild-type amino acids; Randomize with bias to one of the amino acids selected from the group consisting of tyrosine, histidine, glutamine, asparagine, lysine, aspartic acid and glutamic acid (approximately 10-100%); Bias to aromatic amino acids (10-100%) |
| j. 95-100h | Randomize but maintain any 5-10 consecutive amino acids as wild-type |
| k. 100a-100o | Randomize but maintain any 5-10 consecutive amino acids as wild-type |

Unless otherwise necessarily implied as a result of logistical considerations, it is to be understood that the various embodiments which relate to choice of amino acids for random, biased or fixed substitution (specified in column 1) as well as the various embodiments related to types of substitutions (column 2) are not mutually exclusive. Moreover the various permutations and combinations of such substitutions are hereby contemplated as embodiments of the invention. For example, substitutions referred to in row a. (any one or more amino acids and preferably all amino acids of residues 100a-100h) #3 (at least approximately 50% wild-type amino acids) may combined with row b. (any one or more and preferably all of amino acids residues 100a, 100b, 100g and 100h) #2 (for instance, at least approximately 90% wild-type amino acids) so that, for instance, any 3 of the amino acids in 100a-100h are biased in favor of wild-type in approximately 50% of the variant $V_H$ ligand-binding fragments and 100a and 100b are biased in favor of wild-type in 90% of potential binding fragments.

By necessary implication the three amino acids that are biased in favor of wild-type are not residues 100a and 100b, but they may be any other three residues. Accordingly, the broadest possible interpretation is to be given to the disclosure of the various combinations and permutations of the embodiments disclosed herein. Furthermore, it is to be understood that each of the various embodiments described herein are disclosed, except insofar as logistically impossible, in reference to each of the various aspects and definitions of the invention. Moreover, it is to be understood that phrases such as at least approximately 10%, or approximately 10-100% are intended to specify a preference for each of the unit percentages between about 7 and 100% that are practically achievable by oligonucleotide primer design and PCR amplification described herein below, as well as other well known PCR techniques and techniques of Controlled Mutation described in the art, and routine variations of such techniques. By the same token, phrases such as at least 80% are intended to specify a preference for each of the unit percentages between 80% and 100%. It is to be understood that biasing of a percentage less than 100% implies unless otherwise implied or stated that the remaining percentage is fully randomized. Furthermore, it is to be understood, for example, that 90% biasing in favor of wild-type amino acids at a given amino acid position is to be approximated by controlling the percentage amounts of each of the three relevant nucleotides (so that, for example, the product of the probabilities of occurrence of the three desired nucleotides in sequence in the growing chain is 90%) so as to supply 90% of correct coding triplet(s) and a total of 10% of random coding triplets, having regard to the degeneracy of the genetic code (for example if two different coding triplets result in a given amino acid, then the sum of the probabilities of achieving those two triplets will have to equal 90%). This is preferably accomplished on an amino acid by amino acid basis so that, for example, the probability of achieving two and three wild-type amino acids in sequence, in the case of 90% biasing is 0.81 and 0.73, respectively, etc. It is to be understood that this high level of biasing may be suitable only for part of the coding sequence into which variability is introduced and that higher levels of biasing are acceptable, when for example substantially all of the amino acids of a long CDR3 are biased, as disclosed in one of embodiments herein.

Accordingly there is a balance to be struck between a large diverse library and biasing for multifactorial characteristics such as solubility. Nevertheless it is contemplated that the library produced may be a pooled library in which several libraries each having varying degrees of biasing to wild-type, for example, 60%, 50%, 40% and 30%, are pooled together to obtain the both desired variability and similarity. The preferred parental binding-fragment may be engineered to maximize the desired characteristic (e.g. solubility, intermolecular interaction) and then made the subject of libraries with varying degrees of biasing. In this connection, the library could be biased to be rich in amino acids, which are highly soluble. It is to be understood that both arms (halves) of the preferred longer loop forming CDR3s may be biased to amino acids that are favored for intermolecular interaction, preferably charged amino acids, so as to provide a method of generating, in addition to loop size, varying loop structures. This bias may be systematically introduced or systematically reduced by randomization, in cooperating pooled libraries having varying degrees of biasing.

With respect to the application of these methods to parental $V_H$, preferably, CDR3s of a variety of different lengths from 16 to 33 amino acids are predominantly represented among the variant $V_H$ ligand-binding fragments. Preferably CDR3s of a variety of different lengths, from 18 to 25 amino acids, or, from 18 to 23 amino acids are predominantly represented in the library. Although the term "predominant" ordinarily implies a majority representation of the specified long CDR3 variant $V_H$ ligand-binding fragments, the invention also contemplates an even less substantial representation, especially within a reasonably large size library (>$10^7$). Preferably, the specified long CDR3 variant $V_H$ ligand-binding fragments have a majority representation within the library and more preferably an even greater or exclusive representation.

Optionally, the parental $V_H$ ligand-binding molecule is reduced in size and the parental $V_H$ ligand-binding molecule is optionally modified by deleting a portion of the CDR2. In another embodiment, CDR3s of the same length as that of the parental $V_H$ ligand-binding molecule are predominantly or exclusively represented in the variant $V_H$ ligand-binding fragments.

In another aspect, the CDR3 region is specifically retained along with human sequence elements of other regions that confer favorable characteristics solubility, to create a phage display library having favorable characteristics of solubility, preferably when compared with variant $V_H$ ligand-binding fragments that have fully randomized hypervariable regions particularly CDR3). In particular, the present inventors have found that favorable solubility characteristics of a parental $V_H$ ligand-binding molecule can be maintained in the population of variant $V_H$ ligand-binding fragments in the course of randomizing the hypervariable regions by biasing all or selected amino acids residues to wild-type and/or biasing in favor of amino acids residues that favor certain or a variety of types of intermolecular interaction. This is respectively accomplished by increasing the percentage amounts of nucleotide bases that represent wild-type amino acids and/or amino acids that provide favorable intermolecular interactions during the randomization procedure e.g. site directed PCR mutagenesis.

Thus, variant $V_H$ ligand-binding fragments having relatively long CDR3s of varying lengths are produced by randomly or partially randomly inserting varying numbers of nucleotide triplets in any part of a randomized portion of the parental $V_H$ framework. Primers of the desired length and nucleotide composition are synthesized followed by PCR amplification. Desired randomization can be achieved by biasing nucleotide composition of the primer. The production of displays of long CDR3 variant binders may also be accomplished by pooling several libraries of variant $V_H$ ligand-binding fragments having randomized or partially randomized CDR3s of different respective uniform lengths. These strategies are not mutually exclusive.

The additional following terms are used herein as follows, unless the context logically implies otherwise:

"Biasing", "biased in favor of" and related forms of these terms are generally intended to refer to weighting in the course of introducing variation in the parental ligand-binding molecule.

"Homologous" or "homology" as used herein refers to "identity" or "similarity" as used in the art, meaning relationships between two or more polynucleotide or amino acid sequences, as determined by comparing the sequences. In the art, identity also means the degree of sequence relatedness between polynucleotide sequences, as the case may be, as determined by the match between strings of such sequences. Both identity and similarity can be readily calculated (Lesk, A. M., ed., *Computational Molecular Biology*, Oxford University Press, New York, 1988; Smith, D. W., ed., *Biocomputing: Informatics and Genome Projects*, Academic Press, New York, 1993; Griffin, A. M., and Griffin, H. G., eds., *Computer Analysis of Sequence Data, Part I*, Humana Press, New Jersey, 1994; von Heinje, G., *Sequence Analysis in Molecular Biology*, Academic Press, 1987; and Gribskov, M. and Devereux, J., eds., *Sequence Analysis Primer*, M Stockton Press, New York, 1991). While there exist a number of methods to measure identity and similarity between two polynucleotide sequences, both terms are well known to skilled artisans (von Heinje, G., 1987; Gribskov, M. and Devereux, J., 1991; and Carillo, H., and Lipman, D., 1988). Methods commonly employed to determine identity or similarity between sequences include, but are not limited to those disclosed in Carillo, H., and Lipman, D. (1988, *SIAM J. Applied Math.*, 48: 1073). Methods to determine identity and similarity are codified in computer programs. Preferred computer program methods to determine identity and similarity between two sequences include, but are not limited to, GCG program package (Devereux, J., et al. (1984), *Nucleic Acids Research* 12(1): 387), BLASTP, BLASTN, and FASTA (Atschul, S. F. et al. (1990), *J. Molec. Biol.* 215: 403). "Percent homology" or "/homologous" or related terms include both of the following interpretations/methods of calculation: 1) an approximate percentage of the sequence referenced in terms of the number of common residues (e.g. 80% of 11 is understood to be an approximation insofar as application of the percentage does not yield a unit number of residues, in which case both the immediately higher number and immediately lower unit numbers, 9 and 8 respectively, are deemed to be covered); 2) the percentage of binding fragments theoretically achievable that have the full wild-type sequence, which is calculated as a product of the probabilities that the wild-type amino acid will occur at a given amino acid position.

"Conserved" regions refer to those which are commonly found in at least other antibodies of the same type or in at least the same species of mammal.

"Wild-type" refers to the parental binding-fragment, which may be a variant of the natural or to the native A6 $V_H$ parental ligand-binding fragment, depending on the context.

"Step-wise" refers to the addition of, for example, nucleic acids, in a manner such that the quantity of nucleic acids added at each step is rigorously control, usually one nucleic acid at a time.

"Spanning" does not preclude deletions or additions within the parental $V_H$ binding-fragment that are not inimical to the operation of the invention.

"Camelid type" refers specifically to one or more features of the camelid VL interface.

"Soluble" includes the generally ascribed meaning in the art and without limitation includes (based on solubility correlated phenomena) the relative amounts of naturally-folded recombinant protein released from the cell.

"Percent biasing" or "% of binding fragments" (or "biasing 10-100%", etc.) refers to biasing on an individual amino acid basis (though other techniques to accomplish the same effect might apparent to those skilled in the art). Similarly, the specification that wild-type amino acids occur at a specified position or series of positions in, for example, at least approximately 50% of potential binding fragments is intended to mean both that 50% biasing is sought at a given such position or that a total of 50% of the correct nucleotide triplets are represented.

"Approximately" in reference to percentages is intended to accommodate attrition of various desired variant $V_H$ ligand-binding fragments, the assumption that the probabilistic outcomes will not be achieved in practice and that certain variation in methods to accomplish the specified results is deemed to be suitable. The term 50% in reference to an uneven number of amino acids residues means that either one more or one less than half of the amino acids is referred to.

The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology (F. M. Ausubel et al., eds., 1987); "PCR: The Polymerase Chain Reaction", (Mullis et al., eds., 1994); "Current Protocols in Immunology" (J. E. Coligan et al., eds., 1991). These references are incorporated herein by reference. These techniques are applicable to the production of the polynucleotides and polypeptides of the invention, and, as such, may be considered in making and practicing the invention. Particularly useful techniques for particular embodiments will be discussed in the sections that follow.

Recombinant genetic techniques have allowed cloning and expression of antibodies, functional fragments thereof and the antigens recognized. These engineered antibodies provide novel methods of production and treatment modalities. For instance, functional immunoglobulin fragments have been expressed in bacteria and transgenic tobacco seeds and plants. Skerra (1993) *Curr. Opin. Immunol.* 5: 256: 262; Fiedler and Conrad (1995) *Bio/Technology* 13: 1090-1093; Zhang et al. (1993) *Cancer Res.* 55: 3384-3591; Ma et al. (1995) *Science* 268: 916; and, for a review of synthetic antibodies, see Barbas (1995) *Nature Med.* 1: 836-839. These and more current references describing these techniques, which these references, particularly those well known to persons practicing in the relevant arts, are hereby incorporated herein by reference.

Nucleotide sequences can be isolated, amplified, and processed by standard recombinant techniques. Standard techniques in the art include digestion with restriction nucleases, and amplification by polymerase chain reaction (PCR), or a suitable combination thereof PCR technology is described in U.S. Pat. Nos. 4,683,195; 4,800,159; 4,754,065; and 4,683, 202, as well as PCR: *The Polymerase Chain Reaction*, Mullis et al., eds., Birkauswer Press, Boston (1994).

In addition to the specific PCR methods of biasing to wild-type A6 amino acid residues detailed below, it is possible to produce multiple different oligonucleotide primers consisting of specified amino acid residues (one or more) of the wild-type A6 molecule (e.g. CDR3 residues), mixing these in appropriate concentrations with a completely randomized (e.g. CDR3) oligonucleotide primer and subjecting the mixture of oligonucleotide primers to PCR. This will result in a biased phage library population of one's choosing (i.e. the amounts of the selectively randomized and totally randomized primers in the mixture will determine the percent of each CDR3 representation in the library).

Polynucleotides comprising a desired sequence can be inserted into a suitable vector, and the vector in turn can be introduced into a suitable host cell for replication and amplification. Polynucleotides can be introduced into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell by standard methods. See, e.g., Sambrook et al. (1989). RNA can also be obtained from transformed host cell, or it can be obtained directly from the DNA by using a DNA-dependent RNA polymerase.

Suitable cloning and expression vectors include any known in the art, e.g., those for use in bacterial, mammalian, yeast and insect expression systems. Specific vectors and suitable host cells are known in the art and are not described in detail herein. See e.g. Gacesa and Ramji, *Vectors*, John Wiley & Sons (1994).

Phage display techniques are generally described or referenced in some of the preceding general references, as well as in U.S. Pat. Nos. 4,593,002; 5,403,484; 5,837,500; 5,571, 698; 5,750,373; 5,821,047; 5,223,409 and 5,702,892. "Phage Display of Peptides and Proteins", (Kay, Brian K. et al., 1996); "Methods in Enzymology", Vol. 267 (Abelson, John N., 1996); "Immunology Methods Manual", (Lefkovits, Ivan, 1997); "Antibody phage display technology and its applications", (Hoogenboom, Hennie R. et al., 1998). *Immunotechnology* 4 p. 1-20; Cesareni G et al. Phage displayed peptide libraries. *Comb Chem High Throughput Screen.* 1999 February; 2(1): 1-17; Yip, Y L et al. Epitope discovery using monoclonal antibodies and phage peptide libraries. *Comb Chem High Throughput Screen.* 1999 June; 2(3): 125-38; Rodi D J et al. Phage-display technology—finding a needle in a vast molecular haystack. *Curr Opin Biotechnol.* 1999 February; 10(1): 87-93.

Generally, DNA encoding millions of variants of a parental binding-fragment can be batch-cloned into the phage genome as a fusion to the gene encoding one of the phage coat proteins (pIII, pVI or pVIII). Upon expression, the coat protein fusion will be incorporated into new phage particles that are assembled in the bacterium. Expression of the fusion product and its subsequent incorporation into the mature phage coat results in the ligand being presented on the phage surface, while its genetic material resides within the phage particle. This connection between ligand genotype and phenotype allows the enrichment of specific phage, e.g. using selection on immobilized target. Phage that display a relevant ligand will be retained, while non-adherent phage will be washed away. Bound phage can be recovered from the surface, reinfected into bacteria and re-grown for further enrichment, and eventually for analysis of binding. The success of ligand phage display hinges on the combination of this display and enrichment method, with the synthesis of large combinatorial repertoires on phage.

While the use of phage is described as an embodiment for the production of libraries for displaying, and selecting particular binding fragments, it is to be understood that and suitable genetic package may be used for the production of libraries of the invention. Such suitable genetic packages include cells, spores and viruses (see U.S. Pat. No. 5,571, 698), or any other suitable replicable genetic packages. With respect to cell based approaches, another popular method of presenting a library is the two-hybrid system (Feilds and Sternglanz, 1994, *Trends in Genetics* 10: 286-292). Those skilled in the art will appreciate that in vitro systems (non-cell based) may be equally applicable to the methods of the present invention, for example ribosome display (Hanes et al., 1998) or RNA-peptide fusion (Mattheakis et al., 1994, Proc Natl Acad Sci USA 91: 9022-26; Hanes et al., 1999, Curr Top Microbiol Immunol 243: 107-22).

Ribosome display is a well documented technique that may be useful for generating libraries. This-entirely in vitro method allows for libraries with a diversity of $>10^{12}$. In this method, a peptide is displayed on the surface of a ribosome that is translating it. Briefly, a library of mRNA molecules (we could start with A6) is translated in vitro translation system to the 3' end, such that the ribosome does not fall off. The protein emerges from the ribosome in such a way that it can fold, but does not fall off. In some instances, there is an additional folding step in an oxiding environment (important for proteins with disulfide bonds). The whole complex of folded protein, ribosome and mRNA, which is stable for several days, can then be panned against a ligand that is recognized by the translated protein. (For example, the translated protein could be an antibody and the ligand is its antigen). The mRNA can then be amplified by reverse transcription and PCR. This technique has been used to successfully generate scFv antibody fragments with high affinity for their target. Reference is made to Hanes, J., Jermutus, L., Weber-Bomhauser, S., Bosshard, H. R. & Pluckthun, A. Ribosome display efficiently selects and evolves high-affinity antibodies in vitro from immune libraries. *Proc. Natl. Acad. Sci. USA* 95, 14130-14135 (1998); Schaffitzel, C., Hanes, J., Jermutus, L. & Pluckthun, A Ribosome display: an in vitro method for selection and evolution of antibodies from libraries. *Journal of Immunological Methods* 231, 119-135 (1999); He, M. et al. Selection of a human anti-progesterone antibody fragment from a transgenic mouse library by ARM ribosome display. *Journal of Immunological Methods* 231, 105-117 (1999); Roberts, R. W. Totally in vitro protein selection using mRNA-protein fusions and ribosome display. *Current Opinion in Chemical Biology* 3, 268-273 (1999); Williams, C. Biotechnology match making: screening orphan ligands and receptors. *Current Opinion in Biotechnology* 11, 42-46 (2000); Mattheakis, L. C., Bhatt, R. R. & Dower, W. J. An in vitro polysome display system for identifying ligands from very large peptide libraries. *Proc. Natl. Acad. Sci. USA* 91, 9022-9026 (1994).

Construction of A6V$_H$-L1 Library

EXAMPLE 1

A dAb phage display library was constructed employing the V$_H$ portion of A6 as a starting template and amino acid substitutions at positions 6, 23, 82a, 93 and 108, as shown in Table 5 below. In addition, silent mutations were introduced in codons for amino acids 3-16 (FR1) to remove a putative recombination site. All mutations were introduced by splice overlap extension—PCR(SOE). The modified V$_H$ was used as a scaffold for complete randomization at positions 100i-100n located at the carboxy terminal of the CDR3 of A6.

TABLE 5

| A6V$_H$-L1 Template | | | | | |
|---|---|---|---|---|---|
| | Position and Amino Acid Identity | | | | |
| Position | 6 | 23 | 82a | 93 | 108 |
| Wild Type A6V$_H$ | E | S | S | V | T |
| Modified A6V$_H$ | A | A | N | A | Q |

Removal of Putative Recombination Site

The codons for amino acids 3-16, which surround the recombination site, were changed. Using the Chi.R/FP and Chi.F/RP primer pairs (Table 6) and pSJF-A6V$_H$ plasmid as template, 5' and 3' fragments were synthesized by PCR in a total volume of 50 µl containing 10 pmol of each primer, 2 mM of each of the four dNTPs, 1× buffer and 2.5 units of AmpliTaq™ DNA polymerase (Perkin Elmer). The PCR protocol consisted of an initial denaturation step at 94° C. for 3 min followed by 30 cycles at 94° C. for 30 sec, 55° C. for 30 sec, 72° C. for 1 min and a final extension step at 72° C. for 10 min. The two fragments were gel purified using the Q1Aquick Gel Extraction™ kit (QIAGEN) and a larger construct was assembled from the 5' and 3' fragments by performing splice overlap extension (SOE) PCR using RP and FP. Briefly, the reaction vial containing both 5' and 3' fragments, 200 µM each of the four dNTPs, 5 µl 10× buffer (NEB), and 2 units of Vent DNA polymerase (NEB) were subjected to 7 cycles of 1 min at 94° C. and 2.5 min at 72° C. To amplify the assembled construct, RP and FP primers were added at a final concentration of 1 pmol/µl and the mixture was subjected to 30 cycles of 1 min at 94° C., 30 sec at 55° C., and 1 min at 72° C. The amplified product was purified (Q1Aquick PCR Purification™ kit) and used as template for the mutagenesis steps. Sequencing revealed that the putative recombination sequences had been removed.

Modification of Positions 6, 23, 82a, 93 and 108

Employing SOE, positions 23, 82a, 93 were mutated initially (Table 5). Using the Chi template, three fragments were synthesised by PCR using the A6V$_H$.S23A.R/A6V$_H$.S82aN/V93A.F (fragment 1), A6V$_H$.S23A.F/RP (fragment 2) and A6V$_H$.V93A.R/FP (fragment 3) primer pairs Crable 6). The first two fragments were assembled by SOE using RP/A6V$_H$.S82aNN93A and the resultant fragment was spliced to the third fragment using RP/FP primers. Sequencing revealed the desired mutations at positions 23, 82a and 93. This product in turn was used as template for the final round of SOE experiments to alter positions 6 and 108. First, two fragments were synthesized using the A6V$_H$.E6A.R/A6V$_H$.T108Q.F and A6V$_H$.E6A.F/RP primer pairs followed by SOE using RP/A6V$_H$.T108Q.F primers. The final construct was purified, digested with BamHI and EcoRI, purified again and ligated to BamHI/EcoRI-restricted expression plasmid. The colonies were then screened to identify clones containing the mutated A6V$_H$.

TABLE 6

PRIMERS USED CHI SITE REMOVAL AND MUTAGENSIS OF A6V$_H$.

Chi.R
CAATTACAAGAAAGTGGTGGCGGACTGGTGCAACCAGGAGGTTCCCTGAGACTC

Chi.F
ACTTTCTTGTAATTGGACCTCGGCCTGCGC

A6VH.S23A.R
CTCTCCTGTGCTGCCTCTGGA

A6VH.S23A.F
TCCAGAGGCAGCACAGGAGAG

A6VH.S82aN/V93A.F
CGCACAGTAATACACAGCCGTGTCCTCAGCTCTCAGACTGTTCATTTGAAGATA

A6VH.V93A.R
GTGTATTACTGTGCGAAAGACAGG

A6VH.E6A.R
CAATTACAAGCTAGTGGTGGC

TABLE 6-continued

PRIMERS USED CHI SITE REMOVAL AND MUTAGENSIS OF A6V$_H$.

A6VH.E6A.F
GCCACCACTAGCTTGTAATTG

A6VH.T108Q.F
TATGGATCCTGAGGAGACGGTGACCTGTGTCCCTTGGCC

A6VH.ApaII.R
CATGACCACAGTGCACAGGAGGTCCAATTACAAGCTAGA

A6VH.NOT.T108Q
CGATTCTGCGGCCGCTGAGGAGACGGTGACCTGTGTCCCTTGGCCCCAGATATC

RP
GCGGATAACAATTTCACACAGGAA

FP
CGCCAGGGTTTTCCCAGTCACGAC

Cloning, Expression and Evaluation of Dimer/Multimer Formation

The modified A6V$_H$, designated A6V$_H$-L1 was cloned into a vector for expression in *E. coli* using EcoR1 and BamH1. Thirty ml of LB containing 100 ug/ml ampicillin was inoculated with a single colony harboring pSJF2-dAb and the culture was shaken at 240 rpm at 37° C. overnight. In the morning the entire overnight culture was used to inoculate 1 liter of M9 medium supplemented with 5 μg/ml vitamin B1, 0.4% casamino acids and 100 μg/ml ampicillin. The culture was shaken at room temperature for 30 hr at 160 rpm and subsequently supplemented with 100 ml of 10× induction medium and 100 ul of 1M isopropylthio-β-D-galactoside. The culture was shaken for another 60 hr, the periplasmic fraction was extracted by osmotic shock method (Anand et al., 1991), and the presence of dAb in the extract was detected by Western blotting (MacKenzie 1994). The periplasmic fraction was dialyzed extensively in 10 mM HEPES (N-[2-hydroxyethyl]piperazine-N' [2-ethanesulfonic acid]) buffer pH 7.0, 500 mM NaCl. The presence of the dAb C-terminal His$_5$ tag allowed a one step protein purification by immobilized metal affinity chromatography using HiTrap Chelating™ column (Phamacia). The 5-ml column was charged with Ni$^{2+}$ by applying 30 ml of a 5 mg/ml NiCl$_2$.6H$_2$O solution and subsequently washed with 15 ml deionized water. Purification was carried out as described (MacKenzie, 1994) except that the starting buffer was 10 mM HEPES buffer, 10 mM imidazole, 500 mM NaCl, pH 7.0, and the bound protein was eluted with a 10-500 mM imidazole gradient. The purity of the protein was determined by SDS-PAGE (Laemmli). To detect the presence of dimer/multimer dAb in the protein preparation, gel filtration chromatography was performed using Superdex75 (Pharmacia) as described (Deng et al., 1995).

Library Construction

A PCR product was generated using A6V$_H$-L1 as template and primers RP and A6V$_H$.Rndm100i-n.F, CCTTGGCCCCAGATATCAAA6[(A/C)NN]GTAATAACCACTACTATC. The latter primer was degenerate in the region encoding residues 100i-n. A second PCR employed 180 pmol of the above product and 100 pmol of each of the two primers A6V$_H$.Apal.R, CATGACCACAGTGCACAGGAGGTCCAATTACAAGCTAG, and A6V$_H$.NotT108Q.F, CGATTCTGCGGCCGCTGAGGAGACGGTGACCTGTGTCCCTTGGCCCCAGATATC. The second set of primers are complimentary to the 5' and 3' ends of the dAb genes and incorporate ApaII and NotI restriction sites (underlined sequences) at the end of the amplified genes. The amplified products were purified, cut sequentially with ApaII and NotI restriction endonucleases, purified again, and ligated to the ApaII/NotI-treated fd-tet phage vector. Following this, 1.5 μg of the desalted ligated product was mixed with 40 μl of competent *E. coli* strain TG1 and the cells were transformed by electroporation. Transformation, library phage amplification and purification and library size determination were performed as described below. The randomization strategy is depicted in FIG. 11.

Library Size Determination.

To determine the size of the library, immediately following the transformation and after the addition of the SOC medium an small aliquot of the electroporated cells were serially diluted in exponentially growing TG1 cells. Two hundred μl of the diluted cells was mixed with 3 ml of 50° C. agarose top and immediately poured onto 2×YT plates pre-warmed to 37° C. Plates were incubated overnight at 37° C. and the number of plaques were used to determine the size of the library.

Panning

Panning was performed using the Nunc-Immuno MaxiSorp™ 8-well strips (Nunc). Briefly, the wells were coated overnight by adding 150 μl of 100 μg/ml antigen in PBS. In the morning, they were rinsed three times with PBS and subsequently blocked with 400 μl PBS-2% (w/v) skim milk (2% MPBS) at 37° C. for 2 hr. The wells were rinsed as above and $10^{12}$ transducing units phage in 2% MPBS were added. The mixture was incubated at room temperature for 1.5 hr after which the unbound phage in the supernatant was removed. The wells were rinsed 10 times with PBS-0.1% (v/v) Tween 20 and then 10 times with PBS to remove the detergent. The bound phage was eluted by adding freshly prepared 200 μl 100 mM triethylamine, pipetting the content of the well up and down several times and incubating the mixture at room temperature for 10 min. The eluted phage was transfered to a tube containing 100 μl 1 M Tris-HCl, pH 7.4 and vortexed to neutralize triethylamine. Following this, 10 ml exponentially growing TG1 culture was infected with 150 μl eluted phage by incubating the mixture at 37° C. for 30 min. Serial dilutions of the infected cells were used to determine the titer of the eluted phage as described in the previous section. The remaining of the infected cells were spun down and then resuspend in 900 μl 2xYT. The cells were mixed in 300 μl aliquots with 3 ml agarose top and the phage propagated on the plates overnight at 37° C. In the morning the phage was purified, the titer was determined, and a total of $10^{11}$ transducing units phage were used for further rounds of selection.

EXAMPLE 2

A library (A6V$_H$-L1a) in which residues 100i and 100n were deleted and residues 95-100h were randomized with 50% biasing in favour of the parental amino acid constitution, was also constructed. The procedure for A6V$_H$-L1a construction was identical to that for A6V$_H$-L1 except that the randomization primer used in the first PCR step was A6V$_H$.95-100hRndm CCCTTGGCCCCAGATATCAAA14[(A/C)NN]TTTCGCACAGTAATACAC. The sequence of the A6V$_H$ for this library is shown in FIG. 12.

EXAMPLE 3

A6V$_H$-L2, a parental V$_H$ ligand binding molecule in which each of positions 6, 23, 74, 82a, 83, 84, 93 and 108 were modified as shown in FIG. 3 relative to the native A6V$_H$ (FIG. 1), was also constructed. Mutations at positions 74, 83 and 84 were introduced with a single mutagenic primer, A6V$_H$.S74A.F, (5'CATTTGAAG-ATACAGAGTGTTCT-TGGCATTGTCTCT3'), which when used together with RP (see Example 1 above) generated an N-terminal fragment. A second primer, A6V$_H$.R83K/A84P.R., (5'TATCTTCAAAT-GAACAGTCTGAAAC-CAGAGGACACGGCT3'), together with FP (see Example 1 above) generated a C-terminal fragment. The two fragments were joined by SOE, using RP and FP as primers, to give the gene encoding A6V$_H$-L2. This molecule showed slightly better levels of monomer production when expressed and assessed by size exclusion chromatography when compared with $A6V_H$-L1.

TABLE 7

Amino acid identity at positions 6, 23, 74, 82a, 83, 84, 93 and 108 for $A6V_H$ and the mutants of $A6V_H$.3

| | Amino acid Identity | | | | | | | |
|---|---|---|---|---|---|---|---|---|
| Kabat # | 6 | 23 | 74 | 82a | 83 | 84 | 93 | 108 |
| A6VH | E | S | S | S | R | A | V | T |
| A6VH-L1 | A | A | S | N | R | A | A | Q |
| A6VH-L2 | A | A | A | N | K | P | A | Q |

EXAMPLE 4

Surface Plasmon Resonance

Binding studies were performed using BIACORE Upgrade (Biacore Inc., Piscataway, N.J.) as described (Jönsson et al., 1991). Approximately 14, 000 RU of anti-FLAG M2 IgG or control IgG were immobilized on CM5 sensor chips by amine coupling. Single-domain antibodies were passed over the sensor chips surfaces in 10 mM HEPES buffer, pH 7.4, 150 mM NaCl, 3.4 mM EDTA, 0.005% P-20 (Biacore Inc.) at 25° C. and at a flow rate of 5 μl/min. Sensorgram data were analyzed using the BIAevaluation 3.0 software package (Biacore Inc.).

EXAMPLE 5

Enzyme-Linked Immunosorbent Assay (ELISA)

Nunc-Immuno MaxiSorp™ plates (Nunc) were coated overnight at 4° C. with 150 μl of 10 μg/ml of 3B1 scFv or BSA in PBS. The contents were removed and the plates were tapped on a paper towel to remove any liquid remaining in the wells. The wells were blocked by adding 300 μl of 2% MPBS and incubating for 2 hr at 37° C. The contents of the wells were emptied as before, 100 μl of purified dAb phage in 2% MPBS was added, and the wells were incubated at room temperature for 1.5 hr. The contents were emptied again and the wells were washed 5 times with PBS-0.05% (v/v) Tween 20 and subsequently blotted on a paper towel to remove any remaining wash buffer. One Hundred μl of recommended dilution of RP/Anti-M13 monoclonal antibody conjugate (Amersham Pharmacia Biotech) in 2% MPBS was added and the wells were incubated at room temperature for 1 hr. The wells were washed six times as before and the binding of dAb to the antigen was detected colorimetrically by adding 100 μl of equal mixtures of TMB Peroxidase Substrate and $H_2O_2$ (Kirkegaard and Perry Laboratories, Gaithersberg, Md., USA) at room temperature for several minutes. The reaction was stopped by adding 100 μl of 1 M $H_3PO_4$ and the $A_{450}$ was measured by DYNATECH MR5000 plate reader (Dynatech Laboratories, Chantilly, Va., USA).

EXAMPLE 6

Introducing Genetic Variation into the Sequence Corresponding to the A6 Heavy Chain CDR3 Region—Randomized Residues Oligonucleotides comprising randomly mutated CDR3 regions were prepared on an Applied Biosystems 394 DNA synthesizer as described above.

1. Production of 23 Randomized Residues (CDR3 1-23):

The anti-codon formula [(A/C)NN] is used resulting in a reduction in possible codon usage from 64 to 32 and reduces the number of possible stop codons. Position one, therefore, comprises only A and C in the synthetic reaction mixture. For complete randomization of the second and third positions of the codons the dNTP mixture comprise 25% each of A,G,C and T.

The 3' oligonucleotide randomizing primer was designed such that the last 15 nucleotides of framework 3 and the first 17 nucleotides of framework 4 were kept constant for hybridization. The nucleotides encoding the intervening amino acids, namely amino acids 1-23 of the CDR3 region were randomized using the following primer: 5' (GTTGTCCCT-TGGCCCCA n[(A/C)NN]TTTCACACAGTAATA] 3' (Where n=23, antisense strand).

Using a 50% A and 50% C for the first nucleotide position for each anti-codon triplet and 25% each of A, C, G, and T for the second and third nucleotide positions for n=23, complete randomization of the 23 amino acids of the A6 CDR3 is achieved.

2. Synthesis of CDRs Comprising 15-23 Residues

The primers are adapted by reducing n to 15-23 in the above primer formulae whilst keeping the flanking nucleotides constant.

3. For Synthesis of CDR3s Comprising 24-33 Residues

The primers would be adapted by increasing n to 24-33 in the above primer formula while keeping the flanking nucleotides constant.

EXAMPLE 7

Selective Randomization Biasing for 50% Homology to Parental Tyrosine

To achieve approximately 50% homology to wild type at any one position in the A6 dAb CDR3 region during antisense synthesis using the DNA synthesizer, the following example would be used. In the case of tyrosine, which is encoded by TAC or TAT (antisense strand GTA or ATA) the nucleotides would be spiked as follows for the antisense strand.
First anticodon nucleotide position: 80% of A and 20% of C is added to the dNTP solution, and G and T are not added to reduce codon degeneracy.
Second anticodon nucleotide position: 80% T and approximately 6.67% of C, 6.67 of A and 6.67% of G.
Third anticodon nucleotide position the mixture: 80% of A and approximately 6.67% of T and 6.67% of G and 6.7% C.
The calculated probability of tyrosine would thus be 0.8×0.8×0.8×100%=51.2%. Thus approximately 51% of the chains of the library will contain a wild-type A6 tyrosine in that specified position.

EXAMPLE 8

Selective Randomization Biasing for 50% Homology to Parental Serine

Using the same strategy in order to achieve approximately 50% homology to wild type serine at one or more positions, the following example is useful.
Using only A and/or C in the first anticodon position the amino acid serine could have two codons these are AGT, TCT and TCG (antisense ACT, AGA and CGA, respectively). The nucleotide spiking levels would be as follows:
First anticodon nucleotide position: 50% A and 50% C.
Second anticodon nucleotide position: 35.35% C, 35.35% G, 14.65% A and 14.65% T
Third anticodon nucleotide position: 35.35% A, 35.35% T, 14.65% C and 14.65% G.
The probability of producing serine for any given fragment, using this strategy is (1×[0.3535+0.3535]×[0.3535+0.3535]×100%=50%. Thus, approximately 50% of the chains will have a serine in the selected position.

EXAMPLE 9

Selective Randomization Biasing for 50% Homology to Parental Serine

To achieve approximately 10% homology to wild type at any one position in the A6 dAb CDR3 region during antisense synthesis using the DNA synthesizer, the following example can be used. In the case of tyrosine which is encoded by TAC or TAT (antisense strand GTA or ATA) the nucleotides would be spiked as follows for the anti sense strand.
First anticodon nucleotide position: 47% of A and 53% of C is added; G and T are not added to reduce codon degeneracy.
Second anticodon nucleotide position: 47% T and approximately 17.67% of C, 17.67 of A and 17.67% of G.
Third anticodon nucleotide position: 47% of A and approximately 17.67% of T and 17.67% of G and 17.67% C.
The calculated probability of tyrosine is thus 0.47×0.47×0.47×100%=10.4%. Thus approximately 10% of the chains of the library will contain a wild-type A6 tyrosine in that specified position.

EXAMPLE 10

Selective Randomization Biasing for 50% Homology to Parental Serine

To achieve approximately 90% homology to wild-type amino acids at any positions in the A6 dAb CDR3 region during antisense synthesis using the DNA synthesizer, the following example would be used. In the case of tyrosine which is encoded by TAC or TAT (antisense strand GTA or ATA) the nucleotides would be spiked as follows:
First anticodon nucleotide position: 97% of A and 3% of C is added, G and T are not added to reduce codon degeneracy. For this reason, only A and C are used in the first anticodon position for all 20 naturally occurring amino acids.
Second antcodon nucleotide position: 97% T and approximately 1% of C, 1% of A and 1% of G.
Third anticodon nucleotide position: 97% of A and approximately 1% of T and 1% of G and 1% C.
The calculated probability of tyrosine would be 0.97×0.97×0.97×100%=91.3%. Thus approximately 90% of the chains of the library will contain a wild-type A6 tyrosine in that specified position.

Using the approaches in the examples above, approximately 10% to approximately 90% of wild type amino acid representation at one or more specified amino acid residues in the A6 CDR3 can be calculated and applied to the DNA synthesizer.

The present invention may be embodied in other specific forms without departing from the spirit or essential characteristics thereof. Certain adaptations and modifications of the invention will be obvious to those skilled in the art. Therefore, the presently discussed embodiments are considered to be illustrative and not restrictive. It is understood that the claims may refer to aspects or embodiments of the invention that are only inferentially referred to in the disclosure. All references disclosed in this application are hereby incorporated by reference.

Additional References:

Anand, N. N., Dubuc, G., Phipps, J., MacKenzie, C. R., Sadowska, J., Young, N. M., Bundle, D. R., and Narang, S. A. (1991). Synthesis and expression in *Escherichia coli* of cistronic DNA encoding an antibody fragment specific for a *Salmonella* serotype B O-antigen. *Gene* 100: 39-44.

Arbabi, G. M., Desmyter, A., Wyns, L., Hamers, R., and Muyldermans, S. (1997). Selection and identification of single domain antibody fragments from camel heavy-chain antibodies. *FEBS Lett* 414: 521-526.

Bodenhausen, G. and Ruben, D. J., Chem. Phys. Lett., 69, 185-188, 1980.

Cai, X. and Garen, A. (1996). A melanoma-specific VH antibody cloned from a fusion phage library of a vaccinated melanoma patient. *Proc Natl Acad Sci USA* 93: 6280-6285.

Chothia, C and Lesk, A. M. (1987). Canonical structures for the hypervariable regions of immunoglobulins. *J Mol Biol* 196: 901-917.

Chothia, C., Novotny, J., Bruccoleri, R., and Karplus, M. (1985). Domain association in immunoglobulin molecules. The packing of variable domains. *J Mol Biol* 186: 651-663.

Clackson, T., Hoogenboom, H. R., Griffiths, A. D., and Winter, G. (1991). Making antibody fragments using phage display libraries. *Nature* 352: 624-628.

Constantine, K. L., Goldfarb, V., Wittekind, M., Anthony, J., Ng, S. C., and Mueller, L. (1992). Sequential 1H and 15N NMR assignments and secondary stricture of a recombinant anti-digoxin antibody VL domain. *Biochemistry* 31: 5033-5043.

Constantine, K. L., Goldfarb, V., Wittekind, M., Friedrichs, M. S., Anthony, J., Ng, S. C., and Mueller, L. (1993). Aliphatic 1H and 13C resonance assignments for the 26-10 antibody VL domain derived from heteronuclear multidimensional NMR spectroscopy. *J Biomol NMR* 3: 41-54.

Dan, M., Earley, E. M., Griffin, M. C., Maiti, P. K., Prashar, A. K., Yuan, X. Y., Friesen, A. D., and Kaplan, H. A. 1995. Human monoclonal antibody BT32/A6 and a cell cycle-independent glioma-associated surface antigen. J. Neurosurg. 82, 475-480.

Davies, J. and Riechmann, L. (1994). 'Camelising' human antibody fragments: NMR studies on VH domains. *FEBS Lett* 339: 285-290.

Davies, J. and Riechmann, L. (1995). Antibody VH domains as small recognition units. *Biotechnology N Y* 13: 475-479.

Davies, J. and Riechmann, L. (1996b). Affinity improvement of single antibody VH domains: residues in all three hypervariable regions affect antigen binding. *Immunotechnology* 2: 169-179.

Davies, J. and Riechmann, L. (1996a). Single antibody domains as small recognition units: design and in vitro antigen selection of camelized, human VH domains with improved protein stability. *Protein Eng* 9: 531-537.

Decanniere, K., Desmyter, A., Lauwereys, M., Ghahroudi, M. A., Muyldermans, S., and Wyns, L. (1999). A single-domain antibody fragment in complex with RNase A: non-canonical loop structures and nanomolar affinity using two CDR loops. *Structure* 7: 361-370.

Delaglio, F., Grzesiek, S., Vuister, G. W., Zhu, G., Pfeifer, J. and Bax, A., J. Biomol. NMR 6, 277-293, 1995.

Deng, S. J., MacKenzie, C. R., Hirama, T., Brousseau, R., Lowary, T. L., Young, N. M., Bundle, D. R., and Narang, S. A. (1995). Basis for selection of improved carbohydrate-binding single-chain antibodies from synthetic gene libraries. *Proc Natl Acad Sci USA* 92: 4992-4996.

Deng, S. J., MacKenzie, C. R., Sadowska, J., Michniewicz, J., Young, N. M., Bundle, D. R., and Narang, S. A. (1994). Selection of antibody single-chain variable fragments with improved carbohydrate binding by phage display. *J Biol Chem* 269: 9533-9538.

Desmyter, A., Transue, T. R, Ghahroudi, M. A., Thi, M. H., Poortmans, F., Hamers, R., Muyldermans, S., and Wyns, L. (1996). Crystal structure of a camel single-domain VH antibody fragment in complex with lysozyme [see comments]. *Nat Struct Biol* 3: 803-811.

Hamers, C. C., Atarhouch, T., Muyldermans, S., Robinson, G., Hamers, C., Songa, E. B., Bendahman, N., and Hamers, R. (1993). Naturally occurring antibodies devoid of light chains. *Nature* 363: 446-448.

Harrison, J. L., Williams, S. C., Winter, G., and Nissim, A. (1996). Screening of phage antibody libraries. *Methods Enzymol* 267: 83-109.

Johnson, B. A. and Blevins, R. A., J. Chem., Phys., 29, 1012-1014, 1994.

Jönsson, U., Fägerstam, L., Ivarsson, B., Johnsson, B., Karlsson, R, Lundh, K, Löfås, S., Persson, B., Roos, H., Rönnberg, I., Sjölander, S., Stenberg, E., Ståhlberg, R., Urbaniczky, C., Östlin, H., and Malmqvist, M. (1991). Real-time biospecific interaction analysis using surface plasmon resonance and a sensor chip technology. BioTechniques 11, 620-627.

Knappik, A. and Pluckthun, A. (1994). An improved affinity tag based on the FLAG peptide for the detection and purification of recombinant antibody fragments. *BioTechniques* 17: 754-761.

Laemmli, U. K. (1970). Cleavage of structural proteins during the assembly of the head of bacteriophage T4. *Nature* 227: 680-685.

Lauwereys, M., Arbabi, G. M., Desmyter, A., Kinne, J., Holzer, W., De Genst, E., Wyns, L., and Muyldermans, S. (1998). Potent enzyme inhibitors derived from dromedary heavy-chain antibodies. *EMBO J* 17: 3512-3520.

Lowman, H. B., Bass, S. H., Simpson, N., and Wells, J. A. (1991). Selecting high-affinity binding proteins by monovalent phage display. *Biochemistry* 30: 10832-10838.

MacKenzie, R. and To, R. (1998). The role of valency in the selection of anti-carbohydrate single-chain Fvs from phage display libraries. *J. Immunol. Methods* 220, 39-49.

MacKenzie, C. R., Sharma, V., Brummell, D., Bilous, D., Dubuc, G., Sadowska, J., Young, N. M., Bundle, D. R., and Narang, S. A. (1994). Effect of C lambda-C kappa domain switching on Fab activity and yield in *Escherichia coli*: synthesis and expression of genes encoding two anti-carbohydrate Fabs. *Biotechnology N Y* 12: 390-395.

MacKenzie, C. R., Hirama, T., Deng, S.-J., Bundle, D. R., Narang, S. A., and Young. N. M. (1996). Analysis by surface plasmon resonance of the influence of valence on the ligand-binding affinity and kinetics of an anti-carbohydrate antibody. J. Biol. Chem. 271, 1527-1533

McAfferty, J., Griffiths, A. D., Winter, G. and Chiswell, D. J. (1990). Nature 348, 552-554.

Messing, J. (1983). New M13 vectors for cloning. Methods in Enzymology 101, 20-78.

Miceli, R. M., Degraaf, M. E., and Fischer, H. D. (1994). Two-stage selection of sequences from a random phage display library delineates both core residues and permitted structural range within an epitope. *J Immunol Methods* 167: 279-287.

Morea, V., Tramontano, A., Rustici, M., Chothia, C., and Lesk, A. M. (1998). Conformations of the third hypervariable region in the VH domain of immunoglobulins. *J Mol Biol* 275: 269-294.

Muyldermans, S., Atarhouch; T., Saldanha, J., Barbosa, J. A., and Hamers, R. (1994). Sequence and structure of VH domain from naturally occurring camel heavy chain immunoglobulins lacking light chains. *Protein Eng* 7: 1129-1135.

Narang, S. A., Yao, F. L., MichnieWics, J. J., Dubuc, G., Phipps, J., and Somorjai, R. L. (1987) Protein Eng. 1, 481-485.

Narang, S. A., Brummell, D. A., Sharma, V., Dubuc, G., MacKenzie, C. R., Michnie Wics, J. J., Sadowska, J., Anand, N., Young, N. M., and Bundle, D. R. (1991) Nucleic Acids Res. Symp. Ser. 24, 173-179.

Nissim, A., Hoogenboom, H. R., Tomlinson, I. M., Flynn, G., Midgley, C., Lane, D., and Winter, G. (1994). Antibody fragments from a 'single pot' phage display library as immunochemical reagents. *EMBO J* 13: 692-698.

Padlan, E. A. (1994). Anatomy of the antibody molecule. *Mol Immunol* 31: 169-217.

Piotto, M., Saudek, V., and Sklenar, V. (1992) *J. Biomol. NMR* 2, 661-665.

Reiter, Y., Schuck, P., Boyd, L. F., and Plaksin, D. (1999). An antibody single-domain phage display library of a native heavy chain variable region: isolation of functional single-domain VH molecules with a unique interface. *J Mol Biol* 290: 685-698.

Sambrook, J. Fritsch E. F. and Maniatis T (1989). "Molecular Cloning: A laboratory Manual ($2^{nd}$ ed.)," Cold Spring Harbor Laboratory, Cold Spring Harbor, N.Y.

Sanger, F., Nicklen, S., and Coulson, A. R. (1977). DNA sequencing with chain-terminating inhibitors. *Proc Natl Acad Sci USA* 74: 5463-5467.

Sheriff, S. and Constantine, K. L. (1996). Redefining the minimal antigen-binding fragment [news; comment]. *Nat Struct Biol* 3: 733-736.

Sklenar, V., Piotto, M., Leppik, R., and Saudek, V. (1993) *J. Magn. Reson. A* 102, 241-245.

Slatter, M., Schleucher, J. and Griesinger, C., Progr. NMR Spectrosc., 1999, 34, 93-158.

Spinelli, S., Frenken, L., Bourgeois, D., de Ron, L., Bos, W., Verrips, T., Anguille, C., Cambillau, C., and Tegoni, M. (1996). The crystal structure of a llama heavy chain variable domain [letter] [see comments]. *Nat Struct Biol* 3: 752-757.

Tung, W. L. and Chow, K. C. (1995). A modified medium for efficient electrotransformation of *E. coli*. *Trends Genet* 11: 128-129.

Vierra, O. and Messing, J. (1982). The pUC plasmids, an M13 mp7-derived system for insertion mutagenesis and sequencing with synthetic universal primers. Gene 19, 259-268.

Vu, K. B., Ghahroudi, M. A., Wyns, L., and Muyldermans, S. (1997). Comparison of llama VH sequences from conventional and heavy chain antibodies. *Mol Immunol* 34: 1121-1131.

Ward, E. S., Gussow, D., Griffiths, A. D., Jones, P. T., and Winter, G. (1989). Binding activities of a repertoire of single immunoglobulin variable domains secreted from *Escherichia coli* [see comments]. *Nature* 341: 544-546.

Wishart, D. S. and Sykes, B. D., J Biomol NMR, 4, 171-180, 1994.

Wishart, D. S., Bigam, C. G., Yao, J., Abildgaard, F., Dyson, H. J., Oldfield, E., Markley, J. L. and Sykes, B. D., J. Biomol. NMR, 6 135-140, 1995.

Zacher, A. N., Stock, C. A., Golden, J. W. and Smith, G. P. (1980). Gene 9, 127-140.

---

We claim:

1. A nucleic acid sequence encoding an immunoglobulin heavy chain variable domain ($V_H$) ligand binding molecule comprising a $V_H$ domain comprising framework regions (FRs) as depicted in SEQ ID NO: 87 or SEQ ID NO: 88, comprising amino acids at positions identified according to the Kabat numbering system wherein position 6 is an alanine, position 23 is an alanine, position 82a is an asparagine, position 93 is an alanine and position 108 is a glutamine.

2. A nucleic acid sequence encoding an immunoglobulin heavy chain variable domain ($V_H$) ligand binding molecule, wherein said $V_H$ ligand binding molecule comprises a $V_H$ domain having at least 90% sequence identity to SEQ ID NO: 87 or SEQ ID NO: 88, and wherein said $V_H$ domain comprises amino acids at positions identified according to the Kabat numbering system wherein position 6 is an alanine, position 23 is an alanine, position 82a is an asparagine, position 93 is an alanine and position 108 is a glutamine.

* * * * *

SEQUENCE LISTING

```
<160> NUMBER OF SEQ ID NOS: 92

<210> SEQ ID NO 1
<211> LENGTH: 6
<212> TYPE: PRT
<213> ORGANISM: Artificial
<220> FEATURE:
<223> OTHER INFORMATION: Randomized region

<400> SEQUENCE: 1

Asp Gln Phe Thr His Ser
1               5

<210> SEQ ID NO 2
<211> LENGTH: 6
<212> TYPE: PRT
<213> ORGANISM: Artificial
<220> FEATURE:
<223> OTHER INFORMATION: Randomized region

<400> SEQUENCE: 2

Ser Ser Met Tyr Gly Asn
1               5

<210> SEQ ID NO 3
<211> LENGTH: 6
<212> TYPE: PRT
<213> ORGANISM: Artificial
<220> FEATURE:
<223> OTHER INFORMATION: Randomized region

<400> SEQUENCE: 3

Ile Lys Met Gln Gln Asn
1               5

<210> SEQ ID NO 4
<211> LENGTH: 6
<212> TYPE: PRT
<213> ORGANISM: Artificial
<220> FEATURE:
<223> OTHER INFORMATION: Randomized region

<400> SEQUENCE: 4

Ser Val Asp Ala Arg Asp
1               5

<210> SEQ ID NO 5
<211> LENGTH: 6
<212> TYPE: PRT
<213> ORGANISM: Artificial
```

<220> FEATURE:
<223> OTHER INFORMATION: Randomized region

<400> SEQUENCE: 5

Val Ser Arg Phe Gly Ala
1               5

<210> SEQ ID NO 6
<211> LENGTH: 6
<212> TYPE: PRT
<213> ORGANISM: Artificial
<220> FEATURE:
<223> OTHER INFORMATION: Randomized region

<400> SEQUENCE: 6

Gly Leu Gly Ser Pro Lys
1               5

<210> SEQ ID NO 7
<211> LENGTH: 6
<212> TYPE: PRT
<213> ORGANISM: Artificial
<220> FEATURE:
<223> OTHER INFORMATION: Randomized region

<400> SEQUENCE: 7

Ile Asp Ala Lys Trp Ala
1               5

<210> SEQ ID NO 8
<211> LENGTH: 6
<212> TYPE: PRT
<213> ORGANISM: Artificial
<220> FEATURE:
<223> OTHER INFORMATION: Randomized region

<400> SEQUENCE: 8

Val Ser Arg Phe Gly Ala
1               5

<210> SEQ ID NO 9
<211> LENGTH: 6
<212> TYPE: PRT
<213> ORGANISM: Artificial
<220> FEATURE:
<223> OTHER INFORMATION: Randomized region

<400> SEQUENCE: 9

His Cys Leu Pro Asp Gly
1               5

<210> SEQ ID NO 10
<211> LENGTH: 6
<212> TYPE: PRT
<213> ORGANISM: Artificial
<220> FEATURE:
<223> OTHER INFORMATION: Randomized region
<220> FEATURE:
<221> NAME/KEY: misc_feature
<222> LOCATION: (4)..(4)
<223> OTHER INFORMATION: Xaa can be any naturally occurring amino acid

<400> SEQUENCE: 10

Arg Trp Arg Xaa Val Pro
1               5

```
<210> SEQ ID NO 11
<211> LENGTH: 6
<212> TYPE: PRT
<213> ORGANISM: Artificial
<220> FEATURE:
<223> OTHER INFORMATION: Randomized region

<400> SEQUENCE: 11

Val Ser Arg Phe Gly Ala
1               5

<210> SEQ ID NO 12
<211> LENGTH: 6
<212> TYPE: PRT
<213> ORGANISM: Artificial
<220> FEATURE:
<223> OTHER INFORMATION: Randomized region

<400> SEQUENCE: 12

Leu Glu Cys Glu Gly Cys
1               5

<210> SEQ ID NO 13
<211> LENGTH: 6
<212> TYPE: PRT
<213> ORGANISM: Artificial
<220> FEATURE:
<223> OTHER INFORMATION: Randomized region

<400> SEQUENCE: 13

Arg Asn Val Gly Ala Leu
1               5

<210> SEQ ID NO 14
<211> LENGTH: 6
<212> TYPE: PRT
<213> ORGANISM: Artificial
<220> FEATURE:
<223> OTHER INFORMATION: Randomized region

<400> SEQUENCE: 14

Arg Arg Ser Asp Tyr Leu
1               5

<210> SEQ ID NO 15
<211> LENGTH: 6
<212> TYPE: PRT
<213> ORGANISM: Artificial
<220> FEATURE:
<223> OTHER INFORMATION: Randomized region

<400> SEQUENCE: 15

Cys Val Arg Gly Ala Glu
1               5

<210> SEQ ID NO 16
<211> LENGTH: 6
<212> TYPE: PRT
<213> ORGANISM: Artificial
<220> FEATURE:
<223> OTHER INFORMATION: Randomized region

<400> SEQUENCE: 16

Ser Pro Ser Leu Ala Ala
1               5
```

```
<210> SEQ ID NO 17
<211> LENGTH: 6
<212> TYPE: PRT
<213> ORGANISM: Artificial
<220> FEATURE:
<223> OTHER INFORMATION: Randomized region

<400> SEQUENCE: 17

His Ala Ser Gly Arg Ser
1               5

<210> SEQ ID NO 18
<211> LENGTH: 6
<212> TYPE: PRT
<213> ORGANISM: Artificial
<220> FEATURE:
<223> OTHER INFORMATION: Randomized region

<400> SEQUENCE: 18

Gly Tyr Met Cys Ser Leu
1               5

<210> SEQ ID NO 19
<211> LENGTH: 6
<212> TYPE: PRT
<213> ORGANISM: Artificial
<220> FEATURE:
<223> OTHER INFORMATION: Randomized region

<400> SEQUENCE: 19

His Asn Lys Asp Leu Ala
1               5

<210> SEQ ID NO 20
<211> LENGTH: 6
<212> TYPE: PRT
<213> ORGANISM: Artificial
<220> FEATURE:
<223> OTHER INFORMATION: Randomized region

<400> SEQUENCE: 20

Leu Ala Asp Leu Tyr Met
1               5

<210> SEQ ID NO 21
<211> LENGTH: 6
<212> TYPE: PRT
<213> ORGANISM: Artificial
<220> FEATURE:
<223> OTHER INFORMATION: Randomized region

<400> SEQUENCE: 21

Trp Arg Arg Ala His Glu
1               5

<210> SEQ ID NO 22
<211> LENGTH: 6
<212> TYPE: PRT
<213> ORGANISM: Artificial
<220> FEATURE:
<223> OTHER INFORMATION: Randomized region

<400> SEQUENCE: 22

Ser Asp Leu Phe Ala Arg
1               5

<210> SEQ ID NO 23
<211> LENGTH: 6
```

```
<212> TYPE: PRT
<213> ORGANISM: Artificial
<220> FEATURE:
<223> OTHER INFORMATION: Randomized region

<400> SEQUENCE: 23

Val Ser Arg Phe Gly Ala
1               5

<210> SEQ ID NO 24
<211> LENGTH: 6
<212> TYPE: PRT
<213> ORGANISM: Artificial
<220> FEATURE:
<223> OTHER INFORMATION: Randomized region

<400> SEQUENCE: 24

Arg Tyr Arg His Ser Thr
1               5

<210> SEQ ID NO 25
<211> LENGTH: 6
<212> TYPE: PRT
<213> ORGANISM: Artificial
<220> FEATURE:
<223> OTHER INFORMATION: Randomized region

<400> SEQUENCE: 25

Ala Arg Leu Ala Gly Pro
1               5

<210> SEQ ID NO 26
<211> LENGTH: 6
<212> TYPE: PRT
<213> ORGANISM: Artificial
<220> FEATURE:
<223> OTHER INFORMATION: Randomized region

<400> SEQUENCE: 26

Ser Tyr Arg Pro Tyr Leu
1               5

<210> SEQ ID NO 27
<211> LENGTH: 6
<212> TYPE: PRT
<213> ORGANISM: Artificial
<220> FEATURE:
<223> OTHER INFORMATION: Randomized region

<400> SEQUENCE: 27

Val Val Leu Gly Asn Ser
1               5

<210> SEQ ID NO 28
<211> LENGTH: 6
<212> TYPE: PRT
<213> ORGANISM: Artificial
<220> FEATURE:
<223> OTHER INFORMATION: motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 28
```

```
Xaa Tyr Lys Xaa Xaa Asp
1               5

<210> SEQ ID NO 29
<211> LENGTH: 36
<212> TYPE: PRT
<213> ORGANISM: Artificial
<220> FEATURE:
<223> OTHER INFORMATION: M-2 Binders
<220> FEATURE:
<221> NAME/KEY: misc_feature
<222> LOCATION: (8)..(12)
<223> OTHER INFORMATION: Xaa can be any naturally occurring amino acid

<400> SEQUENCE: 29

Glu Val Gln Leu Gln Ala Ser Xaa Xaa Xaa Xaa Xaa Ser Gly Tyr Tyr
1               5                   10                  15

Glu Asp Asp Tyr Arg Leu Phe Asp Ile Trp Gly Gln Gly Thr Gln Val
            20                  25                  30

Thr Val Ser Ser
        35

<210> SEQ ID NO 30
<211> LENGTH: 48
<212> TYPE: PRT
<213> ORGANISM: Artificial
<220> FEATURE:
<223> OTHER INFORMATION: M-2 Binders
<220> FEATURE:
<221> NAME/KEY: misc_feature
<222> LOCATION: (15)..(19)
<223> OTHER INFORMATION: Xaa can be any naturally occurring amino acid

<400> SEQUENCE: 30

Glu Val Gln Leu Gln Ala Ser Gly Gly Gly Leu Val Gln Pro Xaa Xaa
1               5                   10                  15

Xaa Xaa Xaa Gly Tyr Tyr Asp Ser Ser Gly Tyr Tyr Lys Asp Leu Asp
            20                  25                  30

Thr Arg Phe Asp Ile Trp Gly Gln Gly Thr Gln Val Thr Val Ser Ser
        35                  40                  45

<210> SEQ ID NO 31
<211> LENGTH: 58
<212> TYPE: PRT
<213> ORGANISM: Artificial
<220> FEATURE:
<223> OTHER INFORMATION: M-2 Binders
<220> FEATURE:
<221> NAME/KEY: misc_feature
<222> LOCATION: (22)..(26)
<223> OTHER INFORMATION: Xaa can be any naturally occurring amino acid

<400> SEQUENCE: 31

Glu Val Gln Leu Gln Ala Ser Gly Gly Gly Leu Val Gln Pro Gly Gly
1               5                   10                  15

Ser Leu Arg Leu Ser Xaa Xaa Xaa Xaa Xaa Arg Leu Lys Val Glu Tyr
            20                  25                  30

Tyr Asp Ser Ser Tyr Tyr Gly Asp His Tyr Lys Trp Phe Asp Ile Trp
        35                  40                  45

Gly Gln Gly Thr Gln Val Thr Val Ser Ser
    50                  55

<210> SEQ ID NO 32
<211> LENGTH: 23
<212> TYPE: PRT
<213> ORGANISM: Artificial
```

```
<220> FEATURE:
<223> OTHER INFORMATION: M-2 Binders

<400> SEQUENCE: 32

Asp Arg Leu Lys Val Glu Tyr Tyr Asp Ser Ser Gly Tyr Tyr Arg Asn
1               5                   10                  15

Glu Tyr Lys Glu Phe Asp Ile
            20

<210> SEQ ID NO 33
<211> LENGTH: 23
<212> TYPE: PRT
<213> ORGANISM: Artificial
<220> FEATURE:
<223> OTHER INFORMATION: M-2 Binders

<400> SEQUENCE: 33

Asp Arg Leu Lys Val Glu Tyr Tyr Asp Ser Ser Gly Tyr Tyr Val Asp
1               5                   10                  15

Glu Tyr Lys Ser Phe Asp Ile
            20

<210> SEQ ID NO 34
<211> LENGTH: 23
<212> TYPE: PRT
<213> ORGANISM: Artificial
<220> FEATURE:
<223> OTHER INFORMATION: M-2 Binders

<400> SEQUENCE: 34

Asp Arg Leu Lys Val Glu Tyr Tyr Asp Ser Ser Gly Tyr Tyr Ala Gly
1               5                   10                  15

Arg Tyr Lys Asp Phe Asp Ile
            20

<210> SEQ ID NO 35
<211> LENGTH: 23
<212> TYPE: PRT
<213> ORGANISM: Artificial
<220> FEATURE:
<223> OTHER INFORMATION: M-2 Binders

<400> SEQUENCE: 35

Asp Arg Leu Lys Val Glu Tyr Tyr Asp Ser Ser Gly Tyr Tyr Arg Ser
1               5                   10                  15

Asp Tyr Lys Arg Phe Asp Ile
            20

<210> SEQ ID NO 36
<211> LENGTH: 23
<212> TYPE: PRT
<213> ORGANISM: Artificial
<220> FEATURE:
<223> OTHER INFORMATION: M-2 Binders

<400> SEQUENCE: 36

Asp Arg Leu Lys Val Glu Tyr Tyr Asp Ser Ser Gly Tyr Tyr Ala Ser
1               5                   10                  15

His Tyr Lys Asp Phe Asp Ile
            20

<210> SEQ ID NO 37
<211> LENGTH: 23
<212> TYPE: PRT
<213> ORGANISM: Artificial
```

```
<220> FEATURE:
<223> OTHER INFORMATION: M-2 Binders

<400> SEQUENCE: 37

Asp Arg Leu Lys Val Glu Tyr Tyr Asp Ser Ser Gly Tyr Tyr Val Asp
1               5                   10                  15

Gly Tyr Lys Asp Phe Asp Ile
            20

<210> SEQ ID NO 38
<211> LENGTH: 23
<212> TYPE: PRT
<213> ORGANISM: Artificial
<220> FEATURE:
<223> OTHER INFORMATION: M-2 Binders

<400> SEQUENCE: 38

Asp Arg Leu Lys Val Glu Tyr Tyr Asp Ser Ser Gly Tyr Tyr Thr Ala
1               5                   10                  15

Asp Tyr Lys Met Phe Asp Ile
            20

<210> SEQ ID NO 39
<211> LENGTH: 23
<212> TYPE: PRT
<213> ORGANISM: Artificial
<220> FEATURE:
<223> OTHER INFORMATION: M-2 Binders

<400> SEQUENCE: 39

Asp Arg Leu Lys Val Glu Tyr Tyr Asp Ser Ser Gly Tyr Tyr Asp Met
1               5                   10                  15

Asp Tyr Lys Thr Phe Asp Ile
            20

<210> SEQ ID NO 40
<211> LENGTH: 23
<212> TYPE: PRT
<213> ORGANISM: Artificial
<220> FEATURE:
<223> OTHER INFORMATION: M-2 Binders
<220> FEATURE:
<221> NAME/KEY: misc_feature
<222> LOCATION: (17)..(17)
<223> OTHER INFORMATION: Xaa can be any naturally occurring amino acid

<400> SEQUENCE: 40

Asp Arg Leu Lys Val Glu Tyr Tyr Asp Ser Ser Gly Tyr Tyr Lys Ser
1               5                   10                  15

Xaa Tyr Lys Ser Phe Asp Ile
            20

<210> SEQ ID NO 41
<211> LENGTH: 23
<212> TYPE: PRT
<213> ORGANISM: Artificial
<220> FEATURE:
<223> OTHER INFORMATION: M-2 Binders

<400> SEQUENCE: 41

Asp Arg Leu Lys Val Glu Tyr Tyr Asp Ser Ser Gly Tyr Tyr Asp Tyr
1               5                   10                  15

Lys Ser Gln Asp Phe Asp Ile
            20
```

```
<210> SEQ ID NO 42
<211> LENGTH: 23
<212> TYPE: PRT
<213> ORGANISM: Artificial
<220> FEATURE:
<223> OTHER INFORMATION: M-2 Binders

<400> SEQUENCE: 42

Asp Arg Leu Lys Val Glu Tyr Tyr Asp Ser Ser Gly Tyr Tyr Asp Tyr
1               5                   10                  15

Lys Ser Gln Asp Phe Asp Ile
            20

<210> SEQ ID NO 43
<211> LENGTH: 23
<212> TYPE: PRT
<213> ORGANISM: Artificial
<220> FEATURE:
<223> OTHER INFORMATION: M-2 Binders

<400> SEQUENCE: 43

Asp Arg Leu Lys Val Glu Tyr Tyr Asp Ser Ser Gly Tyr Tyr Lys Asp
1               5                   10                  15

Trp Asp Ser Ser Phe Asp Ile
            20

<210> SEQ ID NO 44
<211> LENGTH: 23
<212> TYPE: PRT
<213> ORGANISM: Artificial
<220> FEATURE:
<223> OTHER INFORMATION: M-2 Binders

<400> SEQUENCE: 44

Asp Arg Leu Lys Val Glu Tyr Tyr Asp Ser Ser Gly Tyr Tyr Lys Asp
1               5                   10                  15

Gly Asp Ser Phe Phe Asp Ile
            20

<210> SEQ ID NO 45
<211> LENGTH: 23
<212> TYPE: PRT
<213> ORGANISM: Artificial
<220> FEATURE:
<223> OTHER INFORMATION: CDR3 Sequence H11 Binders
<220> FEATURE:
<221> NAME/KEY: misc_feature
<222> LOCATION: (13)..(14)
<223> OTHER INFORMATION: Xaa can be any naturally occurring amino acid

<400> SEQUENCE: 45

Asp Arg Leu Lys Val Glu Tyr Tyr Asp Ser Ser Gly Xaa Xaa Tyr Ser
1               5                   10                  15

Phe Ser Ser Pro Phe Asp Ile
            20

<210> SEQ ID NO 46
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 46

Asp Arg Leu Lys Val Glu Tyr Tyr Asp Ser Ser Gly Tyr Tyr Tyr Asp
1               5                   10                  15
```

Phe Ser Ser Pro Phe Asp Ile
            20

<210> SEQ ID NO 47
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 47

Asp Arg Leu Lys Val Glu Tyr Tyr Asp Ser Ser Gly Tyr Tyr Asn Leu
1               5                   10                  15

Phe Ser Ser Pro Phe Asp Ile
            20

<210> SEQ ID NO 48
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 48

Asp Arg Leu Lys Val Glu Tyr Tyr Asp Ser Ser Gly Tyr Tyr Ser Glu
1               5                   10                  15

Phe Ser Ser Pro Phe Asp Ile
            20

<210> SEQ ID NO 49
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 49

Asp Arg Leu Lys Val Glu Tyr Tyr Asp Ser Ser Gly Tyr Tyr Ser Asp
1               5                   10                  15

Phe Ser Ser Pro Phe Asp Ile
            20

<210> SEQ ID NO 50
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 50

Asp Arg Leu Lys Val Glu Tyr Tyr Asp Ser Ser Gly Tyr Tyr Thr Asp
1               5                   10                  15

Met Ser Trp Glu Phe Asp Ile
            20

<210> SEQ ID NO 51
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 51

Asp Arg Leu Lys Val Glu Tyr Tyr Asp Ser Ser Gly Tyr Tyr Asp Leu
1               5                   10                  15

-continued

Gly Ser Trp Glu Phe Asp Ile
            20

<210> SEQ ID NO 52
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 52

Asp Arg Leu Lys Val Glu Tyr Tyr Asp Ser Ser Gly Tyr Tyr Asp Tyr
1               5                   10                  15

Val Ser Trp Glu Phe Asp Ile
            20

<210> SEQ ID NO 53
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 53

Asp Arg Leu Lys Val Glu Tyr Tyr Asp Ser Ser Gly Tyr Tyr Asp Trp
1               5                   10                  15

Gly Ser Trp Thr Phe Asp Ile
            20

<210> SEQ ID NO 54
<211> LENGTH: 23
<212> TYPE: PRT
<213> ORGANISM: Artificial
<220> FEATURE:
<223> OTHER INFORMATION: CDR3 Sequence H11 Binders
<220> FEATURE:
<221> NAME/KEY: misc_feature
<222> LOCATION: (17)..(17)
<223> OTHER INFORMATION: Xaa can be any naturally occurring amino acid

<400> SEQUENCE: 54

Asp Arg Leu Lys Val Glu Tyr Tyr Asp Ser Ser Gly Tyr Tyr Asp Gly
1               5                   10                  15

Xaa Thr Trp Asp Phe Asp Ile
            20

<210> SEQ ID NO 55
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 55

Asp Arg Leu Lys Val Glu Tyr Tyr Asp Ser Ser Gly Tyr Tyr Trp Glu
1               5                   10                  15

Gly Ser Gly Leu Phe Asp Ile
            20

<210> SEQ ID NO 56
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 56

```
Asp Arg Leu Lys Val Glu Tyr Tyr Asp Ser Ser Gly Tyr Tyr Ile Trp
1               5                   10                  15

Tyr Ser Gly Leu Phe Asp Ile
            20

<210> SEQ ID NO 57
<211> LENGTH: 23
<212> TYPE: PRT
<213> ORGANISM: Artificial
<220> FEATURE:
<223> OTHER INFORMATION: CDR3 Sequence H11 Binders

<400> SEQUENCE: 57

Asp Arg Leu Lys Val Glu Tyr Tyr Asp Ser Ser Gly Tyr Tyr Ser Ser
1               5                   10                  15

Trp Ala Ser Ala Phe Asp Ile
            20

<210> SEQ ID NO 58
<211> LENGTH: 6
<212> TYPE: PRT
<213> ORGANISM: Artificial
<220> FEATURE:
<223> OTHER INFORMATION: dAb designated Yst9.1-L3-9

<400> SEQUENCE: 58

Val Ser Arg Phe Gly Ala
1               5

<210> SEQ ID NO 59
<211> LENGTH: 54
<212> TYPE: DNA
<213> ORGANISM: Artificial
<220> FEATURE:
<223> OTHER INFORMATION: Primer

<400> SEQUENCE: 59
caattacaag aaagtggtgg cggactggtg caaccaggag gttccctgag actc         54

<210> SEQ ID NO 60
<211> LENGTH: 30
<212> TYPE: DNA
<213> ORGANISM: Artificial
<220> FEATURE:
<223> OTHER INFORMATION: Primer

<400> SEQUENCE: 60
actttcttgt aattggacct cggcctgcgc                                    30

<210> SEQ ID NO 61
<211> LENGTH: 21
<212> TYPE: DNA
<213> ORGANISM: Artificial
<220> FEATURE:
<223> OTHER INFORMATION: Primer

<400> SEQUENCE: 61
ctctcctgtg ctgcctctgg a                                             21

<210> SEQ ID NO 62
<211> LENGTH: 21
<212> TYPE: DNA
<213> ORGANISM: Artificial
<220> FEATURE:
<223> OTHER INFORMATION: Primer
```

-continued

<400> SEQUENCE: 62
tccagaggca gcacaggaga g                                              21

<210> SEQ ID NO 63
<211> LENGTH: 54
<212> TYPE: DNA
<213> ORGANISM: Artificial
<220> FEATURE:
<223> OTHER INFORMATION: Primer

<400> SEQUENCE: 63
cgcacagtaa tacacagccg tgtcctcagc tctcagactg ttcatttgaa gata          54

<210> SEQ ID NO 64
<211> LENGTH: 24
<212> TYPE: DNA
<213> ORGANISM: Artificial
<220> FEATURE:
<223> OTHER INFORMATION: Primer

<400> SEQUENCE: 64
gtgtattact gtgcgaaaga cagg                                           24

<210> SEQ ID NO 65
<211> LENGTH: 21
<212> TYPE: DNA
<213> ORGANISM: Artificial
<220> FEATURE:
<223> OTHER INFORMATION: Primer

<400> SEQUENCE: 65
caattacaag ctagtggtgg c                                              21

<210> SEQ ID NO 66
<211> LENGTH: 21
<212> TYPE: DNA
<213> ORGANISM: Artificial
<220> FEATURE:
<223> OTHER INFORMATION: Primer

<400> SEQUENCE: 66
gccaccacta gcttgtaatt g                                              21

<210> SEQ ID NO 67
<211> LENGTH: 39
<212> TYPE: DNA
<213> ORGANISM: Artificial
<220> FEATURE:
<223> OTHER INFORMATION: Primer

<400> SEQUENCE: 67
tatggatcct gaggagacgg tgacctgtgt cccttggcc                           39

<210> SEQ ID NO 68
<211> LENGTH: 39
<212> TYPE: DNA
<213> ORGANISM: Artificial
<220> FEATURE:
<223> OTHER INFORMATION: Primer

<400> SEQUENCE: 68
catgaccaca gtgcacagga ggtccaatta caagctaga                           39

<210> SEQ ID NO 69
<211> LENGTH: 54
<212> TYPE: DNA

<213> ORGANISM: Artificial
<220> FEATURE:
<223> OTHER INFORMATION: Primer

<400> SEQUENCE: 69
cgattctgcg gccgctgagg agacggtgac ctgtgtccct tggccccaga tatc    54

<210> SEQ ID NO 70
<211> LENGTH: 24
<212> TYPE: DNA
<213> ORGANISM: Artificial
<220> FEATURE:
<223> OTHER INFORMATION: Primer

<400> SEQUENCE: 70
gcggataaca atttcacaca ggaa    24

<210> SEQ ID NO 71
<211> LENGTH: 24
<212> TYPE: DNA
<213> ORGANISM: Artificial
<220> FEATURE:
<223> OTHER INFORMATION: Primer

<400> SEQUENCE: 71
cgccagggtt ttcccagtca cgac    24

<210> SEQ ID NO 72
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: n is a or c
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: n is a or c
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: n is a or c
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (30)..(30)
<223> OTHER INFORMATION: n is a or c
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (33)..(33)
<223> OTHER INFORMATION: n is a or c
<220> FEATURE:
<221> NAME/KEY: misc_feature
<222> LOCATION: (34)..(35)
<223> OTHER INFORMATION: n is a, c, g, or t
<220> FEATURE:

```
<221> NAME/KEY: misc_feature
<222> LOCATION: (36)..(36)
<223> OTHER INFORMATION: n is a or c
<220> FEATURE:
<221> NAME/KEY: misc_feature
<222> LOCATION: (37)..(38)
<223> OTHER INFORMATION: n is a, c, g, or t

<400> SEQUENCE: 72
ccttggcccc agatatcaaa nnnnnnnnnn nnnnnnnngt aataaccact actatc         56

<210> SEQ ID NO 73
<211> LENGTH: 38
<212> TYPE: DNA
<213> ORGANISM: Artificial
<220> FEATURE:
<223> OTHER INFORMATION: Primer

<400> SEQUENCE: 73
catgaccaca gtgcacagga ggtccaatta caagctag                             38

<210> SEQ ID NO 74
<211> LENGTH: 54
<212> TYPE: DNA
<213> ORGANISM: Artificial
<220> FEATURE:
<223> OTHER INFORMATION: Primer

<400> SEQUENCE: 74
cgattctgcg gccgctgagg agacggtgac ctgtgtccct tggccccaga tatc           54

<210> SEQ ID NO 75
<211> LENGTH: 81
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (22)..(22)
<223> OTHER INFORMATION: n is a or c
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: n is a or c
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: n is a or c
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: n is a or c
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: n is a or c
<220> FEATURE:
```

```
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(37)
<223> OTHER INFORMATION: n is a or c
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (40)..(40)
<223> OTHER INFORMATION: n is a or c
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (43)..(43)
<223> OTHER INFORMATION: n is a or c
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (46)..(46)
<223> OTHER INFORMATION: n is a or c
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (49)..(49)
<223> OTHER INFORMATION: n is a or c
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (52)..(52)
<223> OTHER INFORMATION: n is a or c
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (55)..(55)
<223> OTHER INFORMATION: n is a or c
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (58)..(58)
<223> OTHER INFORMATION: n is a or c
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (61)..(61)
<223> OTHER INFORMATION: n is a or c
<220> FEATURE:
<221> NAME/KEY: misc_feature
<222> LOCATION: (62)..(63)
<223> OTHER INFORMATION: n is a, c, g, or t

<400> SEQUENCE: 75
cccttggccc cagatatcaa annnnnnnnn nnnnnnnnnn nnnnnnnnnn nnnnnnnnnn      60
```

```
nnntttcgca cagtaataca c                                                    81
```

<210> SEQ ID NO 76
<211> LENGTH: 37
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (10)..(10)
<223> OTHER INFORMATION: n is a, c, g, or t

<400> SEQUENCE: 76

```
catttgaagn atacagagtg ttcttggcat tgtctct                                   37
```

<210> SEQ ID NO 77
<211> LENGTH: 40
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (26)..(26)
<223> OTHER INFORMATION: n is a, c, g, or t

<400> SEQUENCE: 77

```
tatcttcaaa tgaacagtct gaaacncaga ggacacggct                                40
```

<210> SEQ ID NO 78
<211> LENGTH: 35
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (17)..(17)
<223> OTHER INFORMATION: n is a or c
<220> FEATURE:
<221> NAME/KEY: misc_feature
<222> LOCATION: (17)..(20)
<223> OTHER INFORMATION: repeated a variable number of times

<400> SEQUENCE: 78

```
gttgtccctt ggccccannn tttcacacag taata                                     35
```

<210> SEQ ID NO 79
<211> LENGTH: 396
<212> TYPE: DNA
<213> ORGANISM: Homo sapiens

<400> SEQUENCE: 79

```
gaggtccagc tgcaggagtc tgggggaggc ttagtccagc ctgggggtc  cctgagactc          60
tcctgttcag cctctggatt caccttcagt agctatgcta tgcactgggt ccgccaggct         120
ccagggaagg gactggaata tgtttcagct attagtagta atggggtag  cacatactac         180
gcagactccg tgaagggcag attcaccatc tccagagaca attccaagaa cactctgtat         240
cttcaaatga gcagtctgag agctgaggac acggctgtgt attactgtgt gaaagacagg         300
ttaaaagtgg agtactatga tagtagtggt tattacgttt ctcggttcgg tgcttttgat         360
atctggggcc aagggacaac ggtcaccgtc tcatca                                   396
```

<210> SEQ ID NO 80
<211> LENGTH: 396
<212> TYPE: DNA

```
<213> ORGANISM: Artificial
<220> FEATURE:
<223> OTHER INFORMATION: Human A6 with modifications

<400> SEQUENCE: 80
gaggtccagc tgcaggcttc tgggggaggc ttagtccagc ctgggggtc  cctgagactc    60 tcctgtgctg cctctggatt caccttcagt agctatgcta tgcactgggt ccgccaggct   120
ccagggaagg gactggaata tgtttcagct attagtagta atgggggtag cacatactac   180
gcagactccg tgaagggcag attcaccatc tccagagaca attccaagaa cactctgtat   240
cttcaaatga acagtctgag agctgaggac acggctgtgt attactgtgc gaaagacagg   300
ttaaaagtgg agtactatga tagtagtggt tattacgttt ctcggttcgg tgcttttgat   360
atctggggcc aagggacaca ggtcaccgtc tcatca                             396

<210> SEQ ID NO 81
<211> LENGTH: 396
<212> TYPE: DNA
<213> ORGANISM: Artificial
<220> FEATURE:
<223> OTHER INFORMATION: Human A6 with modifications

<400> SEQUENCE: 81
gaggtccagc tgcaggcttc tgggggaggc ttagtccagc ctgggggtc  cctgagactc    60 tcctgtgctg cctctggatt caccttcagt agctatgcta tgcactgggt ccgccaggct   120
ccagggaagg gactggaata tgtttcagct attagtagta atgggggtag cacatactac   180
gcagactccg tgaagggcag attcaccatc tccagagaca atgccaagaa cactctgtat   240
cttcaaatga acagtctgaa accagaggac acggctgtgt attactgtgc gaaagacagg   300
ttaaaagtgg agtactatga tagtagtggt tattacgttt ctcggttcgg tgcttttgat   360
atctggggcc aagggacaca ggtcaccgtc tcatca                             396

<210> SEQ ID NO 82
<211> LENGTH: 396
<212> TYPE: DNA
<213> ORGANISM: Artificial
<220> FEATURE:
<223> OTHER INFORMATION: Human A6 with modifications

<400> SEQUENCE: 82
gaggtccaat tacaggaaag tggtggcgga ctggtgcaac caggaggatc cctgagactc    60
tcctgttcag cctctggatt caccttcagt agctatgcta tgcactgggt ccgccaggct   120
ccagggaagg gactggaata tgtttcagct attagtagta atgggggtag cacatactac   180
gcagactccg tgaagggcag attcaccatc tccagagaca attccaagaa cactctgtat   240
cttcaaatga gcagtctgag agctgaggac acggctgtgt attactgtgt gaaagacagg   300
ttaaaagtgg agtactatga tagtagtggt tattacgttt ctcggttcgg tgcttttgat   360
atctggggcc aagggacaac ggtcaccgtc tcatca                             396

<210> SEQ ID NO 83
<211> LENGTH: 396
<212> TYPE: DNA
<213> ORGANISM: Artificial
<220> FEATURE:
<223> OTHER INFORMATION: Human A6 with modifications

<400> SEQUENCE: 83
gaggtccagc tgcaggagtc tgggggaggc ttagtccagc ctgggggtc  cctgagactc    60
```

```
tcctgttcag cctctggatt caccttcagt agctatgcta tgcactgggt ccgccaggct      120
ccagggaagg aacgtgaagg tgtttcagct attagtagta atgggggtag cacatactac      180
gcagactccg tgaagggcag attcaccatc tccagagaca attccaagaa cactctgtat      240
cttcaaatga gcagtctgag agctgaggac acggctgtgt attactgtgc agcagacagg      300
ttaaaagtgg agtactatga tagtagtggt tattacgttt ctcggttcgg tgcttttgat      360
atctggggcc aagggacaac ggtcaccgtc tcatca                                396

<210> SEQ ID NO 84
<211> LENGTH: 396
<212> TYPE: DNA
<213> ORGANISM: Artificial
<220> FEATURE:
<223> OTHER INFORMATION: Human A6 with modifications
<220> FEATURE:
<221> NAME/KEY: misc_feature
<222> LOCATION: (337)..(338)
<223> OTHER INFORMATION: n is a, c, g, or t
<220> FEATURE:
<221> NAME/KEY: misc_feature
<222> LOCATION: (339)..(339)
<223> OTHER INFORMATION: n is a or c
<220> FEATURE:
<221> NAME/KEY: misc_feature
<222> LOCATION: (340)..(341)
<223> OTHER INFORMATION: n is a, c, g, or t
<220> FEATURE:
<221> NAME/KEY: misc_feature
<222> LOCATION: (342)..(342)
<223> OTHER INFORMATION: n is a or c
<220> FEATURE:
<221> NAME/KEY: misc_feature
<222> LOCATION: (343)..(344)
<223> OTHER INFORMATION: n is a, c, g, or t
<220> FEATURE:
<221> NAME/KEY: misc_feature
<222> LOCATION: (345)..(345)
<223> OTHER INFORMATION: n is a or c
<220> FEATURE:
<221> NAME/KEY: misc_feature
<222> LOCATION: (346)..(347)
<223> OTHER INFORMATION: n is a, c, g, or t
<220> FEATURE:
<221> NAME/KEY: misc_feature
<222> LOCATION: (348)..(348)
<223> OTHER INFORMATION: n is a or c
<220> FEATURE:
<221> NAME/KEY: misc_feature
<222> LOCATION: (349)..(350)
<223> OTHER INFORMATION: n is a, c, g, or t
<220> FEATURE:
<221> NAME/KEY: misc_feature
<222> LOCATION: (351)..(351)
<223> OTHER INFORMATION: n is a or c
<220> FEATURE:
<221> NAME/KEY: misc_feature
<222> LOCATION: (352)..(353)
<223> OTHER INFORMATION: n is a, c, g, or t
<220> FEATURE:
<221> NAME/KEY: misc_feature
<222> LOCATION: (354)..(354)
<223> OTHER INFORMATION: n is a or c

<400> SEQUENCE: 84
gaggtccaat tacaagctag tggtggcgga ctggtgcaac caggaggttc cctgagactc       60
tcctgtgctg cctctggatt caccttcagt agctatgcta tgcactgggt ccgccaggct      120
ccagggaagg gactggaata tgtttcagct attagtagta atgggggtag cacatactac      180
gcagactccg tgaagggcag attcaccatc tccagagaca attccaagaa cactctgtat      240
cttcaaatga acagtctgag agctgaggac acggctgtgt attactgtgc gaaagacagg      300
```

```
ttaaaagtgg agtactatga tagtagtggt tattacnnnn nnnnnnnnnn nnnntttgat    360
atctggggcc aagggacaca ggtcaccgtc tcctca                              396
```

<210> SEQ ID NO 85
<211> LENGTH: 378
<212> TYPE: DNA
<213> ORGANISM: Artificial
<220> FEATURE:
<223> OTHER INFORMATION: Human A6 with modifications
<220> FEATURE:
<221> NAME/KEY: misc_feature
<222> LOCATION: (295)..(296)
<223> OTHER INFORMATION: n is a, c, g, or t, at least 50% biased in favour of wild type amino acid
<220> FEATURE:
<221> NAME/KEY: misc_feature
<222> LOCATION: (297)..(297)
<223> OTHER INFORMATION: n is a or c, at least 50% biased in favour of wild type amino acid
<220> FEATURE:
<221> NAME/KEY: misc_feature
<222> LOCATION: (298)..(299)
<223> OTHER INFORMATION: n is a, c, g, or t, at least 50% biased in favour of wild type amino acid
<220> FEATURE:
<221> NAME/KEY: misc_feature
<222> LOCATION: (300)..(300)
<223> OTHER INFORMATION: n is a or c, at least 50% biased in favour of wild type amino acid
<220> FEATURE:
<221> NAME/KEY: misc_feature
<222> LOCATION: (301)..(302)
<223> OTHER INFORMATION: n is a, c, g, or t, at least 50% biased in favour of wild type amino acid
<220> FEATURE:
<221> NAME/KEY: misc_feature
<222> LOCATION: (303)..(303)
<223> OTHER INFORMATION: n is a or c, at least 50% biased in favour of wild type amino acid
<220> FEATURE:
<221> NAME/KEY: misc_feature
<222> LOCATION: (304)..(305)
<223> OTHER INFORMATION: n is a, c, g, or t, at least 50% biased in favour of wild type amino acid
<220> FEATURE:
<221> NAME/KEY: misc_feature
<222> LOCATION: (306)..(306)
<223> OTHER INFORMATION: n is a or c, at least 50% biased in favour of wild type amino acid
<220> FEATURE:
<221> NAME/KEY: misc_feature
<222> LOCATION: (307)..(308)
<223> OTHER INFORMATION: n is a, c, g, or t, at least 50% biased in favour of wild type amino acid
<220> FEATURE:
<221> NAME/KEY: misc_feature
<222> LOCATION: (309)..(309)
<223> OTHER INFORMATION: n is a or c, at least 50% biased in favour of wild type amino acid
<220> FEATURE:
<221> NAME/KEY: misc_feature
<222> LOCATION: (310)..(311)
<223> OTHER INFORMATION: n is a, c, g, or t, at least 50% biased in favour of wild type amino acid
<220> FEATURE:
<221> NAME/KEY: misc_feature
<222> LOCATION: (312)..(312)
<223> OTHER INFORMATION: n is a or c, at least 50% biased in favour of wild type amino acid
<220> FEATURE:
<221> NAME/KEY: misc_feature
<222> LOCATION: (313)..(314)
<223> OTHER INFORMATION: n is a, c, g, or t, at least 50% biased in favour of wild type amino acid
<220> FEATURE:
<221> NAME/KEY: misc_feature
<222> LOCATION: (315)..(315)
<223> OTHER INFORMATION: n is a or c, at least 50% biased in favour of

```
      wild type amino acid
<220> FEATURE:
<221> NAME/KEY: misc_feature
<222> LOCATION: (316)..(317)
<223> OTHER INFORMATION: n is a, c, g, or t, at least 50% biased in
      favour of wild type amino acid
<220> FEATURE:
<221> NAME/KEY: misc_feature
<222> LOCATION: (318)..(318)
<223> OTHER INFORMATION: n is a or c, at least 50% biased in favour of
      wild type amino acid
<220> FEATURE:
<221> NAME/KEY: misc_feature
<222> LOCATION: (319)..(320)
<223> OTHER INFORMATION: n is a, c, g, or t, at least 50% biased in
      favour of wild type amino acid
<220> FEATURE:
<221> NAME/KEY: misc_feature
<222> LOCATION: (321)..(321)
<223> OTHER INFORMATION: n is a or c, at least 50% biased in favour of
      wild type amino acid
<220> FEATURE:
<221> NAME/KEY: misc_feature
<222> LOCATION: (322)..(323)
<223> OTHER INFORMATION: n is a, c, g, or t, at least 50% biased in
      favour of wild type amino acid
<220> FEATURE:
<221> NAME/KEY: misc_feature
<222> LOCATION: (324)..(324)
<223> OTHER INFORMATION: n is a or c, at least 50% biased in favour of
      wild type amino acid
<220> FEATURE:
<221> NAME/KEY: misc_feature
<222> LOCATION: (325)..(326)
<223> OTHER INFORMATION: n is a, c, g, or t, at least 50% biased in
      favour of wild type amino acid
<220> FEATURE:
<221> NAME/KEY: misc_feature
<222> LOCATION: (327)..(327)
<223> OTHER INFORMATION: n is a or c, at least 50% biased in favour of
      wild type amino acid
<220> FEATURE:
<221> NAME/KEY: misc_feature
<222> LOCATION: (328)..(329)
<223> OTHER INFORMATION: n is a, c, g, or t, at least 50% biased in
      favour of wild type amino acid
<220> FEATURE:
<221> NAME/KEY: misc_feature
<222> LOCATION: (330)..(330)
<223> OTHER INFORMATION: n is a or c, at least 50% biased in favour of
      wild type amino acid
<220> FEATURE:
<221> NAME/KEY: misc_feature
<222> LOCATION: (331)..(332)
<223> OTHER INFORMATION: n is a, c, g, or t, at least 50% biased in
      favour of wild type amino acid
<220> FEATURE:
<221> NAME/KEY: misc_feature
<222> LOCATION: (333)..(333)
<223> OTHER INFORMATION: n is a or c, at least 50% biased in favour of
      wild type amino acid
<220> FEATURE:
<221> NAME/KEY: misc_feature
<222> LOCATION: (334)..(335)
<223> OTHER INFORMATION: n is a, c, g, or t, at least 50% biased in
      favour of wild type amino acid
<220> FEATURE:
<221> NAME/KEY: misc_feature
<222> LOCATION: (336)..(336)
<223> OTHER INFORMATION: n is a or c, at least 50% biased in favour of
      wild type amino acid

<400> SEQUENCE: 85
gaggtccaat tacaagctag tggtggcgga ctggtgcaac caggaccttc cctgagactc      60
tcctgtgctg cctctggatt caccttcagt agctatgcta tgcactgggt ccgccaggct     120
ccagggaagg gactggaata tgtttcagct attagtagta atgggggtag cacatactac     180
```

```
gcagactccg tgaagggcag attcaccatc tccagagaca attccaagaa cactctgtat    240
cttcaaatga acagtctgag agctgaggac acggctgtgt attactgtgg gaaannnnnn    300
nnnnnnnnnn nnnnnnnnnn nnnnnnnnnn nnnnnntttg atatctgggg ccaagggaca    360
caggtcaccg tctcctca                                                  378
```

<210> SEQ ID NO 86
<211> LENGTH: 132
<212> TYPE: PRT
<213> ORGANISM: Homo sapiens

<400> SEQUENCE: 86

Glu Val Gln Leu Gln Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Asp Arg Leu Lys Val Glu Tyr Tyr Asp Ser Ser Gly Tyr Tyr
            100                 105                 110

Val Ser Arg Phe Gly Ala Phe Asp Ile Trp Gly Gln Gly Thr Thr Val
        115                 120                 125

Thr Val Ser Ser
    130

<210> SEQ ID NO 87
<211> LENGTH: 132
<212> TYPE: PRT
<213> ORGANISM: Artificial
<220> FEATURE:
<223> OTHER INFORMATION: Human A6 with modifications

<400> SEQUENCE: 87

Glu Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Lys Val Glu Tyr Tyr Asp Ser Ser Gly Tyr Tyr
            100                 105                 110

Val Ser Arg Phe Gly Ala Phe Asp Ile Trp Gly Gln Gly Thr Gln Val
        115                 120                 125

Thr Val Ser Ser
    130

```
<210> SEQ ID NO 88
<211> LENGTH: 132
<212> TYPE: PRT
<213> ORGANISM: Artificial
<220> FEATURE:
<223> OTHER INFORMATION: Human A6 with modifications

<400> SEQUENCE: 88

Glu Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Arg Leu Lys Val Glu Tyr Tyr Asp Ser Ser Gly Tyr Tyr
            100                 105                 110

Val Ser Arg Phe Gly Ala Phe Asp Ile Trp Gly Gln Gly Thr Gln Val
        115                 120                 125

Thr Val Ser Ser
    130

<210> SEQ ID NO 89
<211> LENGTH: 132
<212> TYPE: PRT
<213> ORGANISM: Artificial
<220> FEATURE:
<223> OTHER INFORMATION: Human A6 with modifications

<400> SEQUENCE: 89

Glu Val Gln Leu Gln Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Asp Arg Leu Lys Val Glu Tyr Tyr Asp Ser Ser Gly Tyr Tyr
            100                 105                 110

Val Ser Arg Phe Gly Ala Phe Asp Ile Trp Gly Gln Gly Thr Thr Val
        115                 120                 125

Thr Val Ser Ser
    130

<210> SEQ ID NO 90
<211> LENGTH: 132
<212> TYPE: PRT
<213> ORGANISM: Artificial
<220> FEATURE:
<223> OTHER INFORMATION: Human A6 with modifications
```

<400> SEQUENCE: 90

Glu Val Gln Leu Gln Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Glu Arg Glu Gly Val
        35                  40                  45

Ser Ala Ile Ser Ser Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ala Asp Arg Leu Lys Val Glu Tyr Tyr Asp Ser Ser Gly Tyr Tyr
                100                 105                 110

Val Ser Arg Phe Gly Ala Phe Asp Ile Trp Gly Gln Gly Thr Thr Val
            115                 120                 125

Thr Val Ser Ser
    130

<210> SEQ ID NO 91
<211> LENGTH: 132
<212> TYPE: PRT
<213> ORGANISM: Artificial
<220> FEATURE:
<223> OTHER INFORMATION: Human A6 with modifications
<220> FEATURE:
<221> NAME/KEY: misc_feature
<222> LOCATION: (113)..(118)
<223> OTHER INFORMATION: Xaa can be any naturally occurring amino acid

<400> SEQUENCE: 91

Glu Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Lys Val Glu Tyr Tyr Asp Ser Ser Gly Tyr Tyr
                100                 105                 110

Xaa Xaa Xaa Xaa Xaa Xaa Phe Asp Ile Trp Gly Gln Gly Thr Gln Val
            115                 120                 125

Thr Val Ser Ser
    130

<210> SEQ ID NO 92
<211> LENGTH: 126
<212> TYPE: PRT
<213> ORGANISM: Artificial
<220> FEATURE:
<223> OTHER INFORMATION: Human A6 with modifications

```
<220> FEATURE:
<221> NAME/KEY: misc_feature
<222> LOCATION: (99)..(112)
<223> OTHER INFORMATION: Xaa can be any naturally occurring amino acid

<400> SEQUENCE: 92

Glu Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Xaa Xaa Xaa Xaa Xaa Xaa Xaa Xaa Xaa Xaa Xaa Xaa Xaa Xaa
            100                 105                 110

Phe Asp Ile Trp Gly Gln Gly Thr Gln Val Thr Val Ser Ser
            115                 120                 125
```